(12) United States Patent
Okusawa et al.

(10) Patent No.: US 10,042,978 B2
(45) Date of Patent: Aug. 7, 2018

(54) MEDICAL SYSTEM

(71) Applicant: OLYMPUS CORPORATION, Hachioji-shi, Tokyo (JP)

(72) Inventors: Yasuhiro Okusawa, Higashimurayama (JP); Koichi Tashiro, Chofu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/171,889

(22) Filed: Jun. 2, 2016

(65) Prior Publication Data
US 2016/0275246 A1  Sep. 22, 2016

Related U.S. Application Data

(63) Continuation of application No. PCT/JP2014/077511, filed on Oct. 16, 2014.

(30) Foreign Application Priority Data

Dec. 11, 2013  (JP) .................................. 2013-256209

(51) Int. Cl.
*A61B 1/00* (2006.01)
*G06F 19/00* (2018.01)
(Continued)

(52) U.S. Cl.
CPC ........ *G06F 19/321* (2013.01); *A61B 1/00009* (2013.01); *A61B 1/00011* (2013.01);
(Continued)

(58) Field of Classification Search
CPC ................ A61B 1/00004; A61B 34/25; A61B 2034/252; A61B 2034/254; G06F 19/325; G06F 19/327
See application file for complete search history.

(56) References Cited

U.S. PATENT DOCUMENTS

2003/0093503 A1  5/2003  Yamaki et al.

FOREIGN PATENT DOCUMENTS

| JP | 2003-164464 A | 6/2003 |
|---|---|---|
| JP | 2011-050653 A | 3/2011 |
| JP | 2012-053750 A | 3/2012 |

OTHER PUBLICATIONS

Jan. 20, 2015 Search Report issued in International Patent Application No. PCT/JP2014/077511.
(Continued)

*Primary Examiner* — Timothy J Neal
*Assistant Examiner* — Aaron B Fairchild
(74) *Attorney, Agent, or Firm* — Oliff PLC

(57) ABSTRACT

A medical system includes: a plurality of medical apparatuses used for surgery using an endoscope; a communication-with-apparatus portion configured to communicate with the plurality of medical apparatuses; a replacement portion configured to replace operation setting values for causing the plurality of medical apparatuses to operate along a procedure for the surgery with progress state information indicating progress of the surgery; a priority degree setting portion configured to set a support priority degree for smoothly advancing surgery, for progress state information; a transmission portion configured to transmit the progress state information; a control apparatus including a communication-with-apparatus portion and the like; and a terminal apparatus including: a receiving portion configured to receive the progress state information transmitted from the transmission portion; and a display portion configured to display the received progress state information.

7 Claims, 20 Drawing Sheets

(51) Int. Cl.
*A61B 34/00* (2016.01)
*A61B 1/04* (2006.01)
*A61B 1/06* (2006.01)
*A61B 1/32* (2006.01)
*A61M 13/00* (2006.01)
*G16H 40/20* (2018.01)
*A61B 18/14* (2006.01)
*A61B 17/00* (2006.01)
*A61B 90/30* (2016.01)

(52) U.S. Cl.
CPC .............. *A61B 1/04* (2013.01); *A61B 1/0661* (2013.01); *A61B 1/32* (2013.01); *A61B 34/25* (2016.02); *A61M 13/003* (2013.01); *G06F 19/325* (2013.01); *G16H 40/20* (2018.01); *A61B 1/00045* (2013.01); *A61B 18/1402* (2013.01); *A61B 90/30* (2016.02); *A61B 2017/00203* (2013.01); *A61B 2034/254* (2016.02); *A61B 2560/0493* (2013.01); *A61M 2202/02* (2013.01); *A61M 2205/3344* (2013.01); *A61M 2205/3375* (2013.01); *A61M 2205/3561* (2013.01); *A61M 2205/3584* (2013.01); *A61M 2205/3592* (2013.01); *A61M 2205/505* (2013.01)

(56) References Cited

OTHER PUBLICATIONS

Oct. 27, 2015 Office Action issued in Japanese Patent Application No. 2015-531389.

Mar. 8, 2016 Decision to Grant issued in Japanese Patent Application No. 2015-531389.

FIG. 4B

| SCENE ITEM | OPERATION SETTING VALUES OF MEDICAL APPARATUSES (OPERATION SETTING STATES) | | | | | |
|---|---|---|---|---|---|---|
| | SHADOWLESS LAMP | PNEUMOPERITONEUM APPARATUS | VIDEO PROCESSOR | LIGHT SOURCE APPARATUS | MONITOR | ELECTRIC KNIFE APPARATUS |
| 1. PREPARATION | OFF | STOP PNEUMOPERITONEUM | ON | LIGHT SOURCE OFF | ON | OUTPUT 0 W |
| 2. ENDOSCOPE INSERTION | ON | START PNEUMOPERITONEUM | → | LIGHT SOURCE ON | → | → |
| 3. GALLBLADDER REMOVAL | OFF | → | → | → | → | OUTPUT 40 W |
| 4. SURGICAL INCISION CLOSING | ON | STOP PNEUMOPERITONEUM | OFF | LIGHT SOURCE OFF | OFF | OUTPUT 0 W |

FIG. 5

| OPERATION MEANS | MICROPHONE (FIRST OPERATION MEANS) | CENTRALIZED OPERATION PANEL (SECOND OPERATION MEANS) |
|---|---|---|
| NURSE NECESSITY DEGREE | HIGH (INSUFFICIENT) | LOW (SUFFICIENT) |
| SUPPORT PRIORITY DEGREE | HIGH | LOW |
| DISPLAY COMMENT | THE NUMBER OF NURSES IS INSUFFICIENT. YOUR SUPPORT IS REQUESTED. | — |

FIG. 6

| ITEM | CONTENT OF DATA |
|---|---|
| OPERATING ROOM NO. | 3 |
| PATIENT'S NAME | TARO TOKYO |
| SURGICAL PROCEDURE | PREPARATION, ENDOSCOPE INSERTION, GALLBLADDER REMOVAL, SURGICAL INCISION CLOSING |
| SELECTED SURGICAL PROCEDURE PHASE | GALLBLADDER REMOVAL |
| SUPPORT PRIORITY DEGREE | HIGH |
| DISPLAY COMMENT | THE NUMBER OF NURSES IS INSUFFICIENT. YOUR SUPPORT IS REQUESTED. |

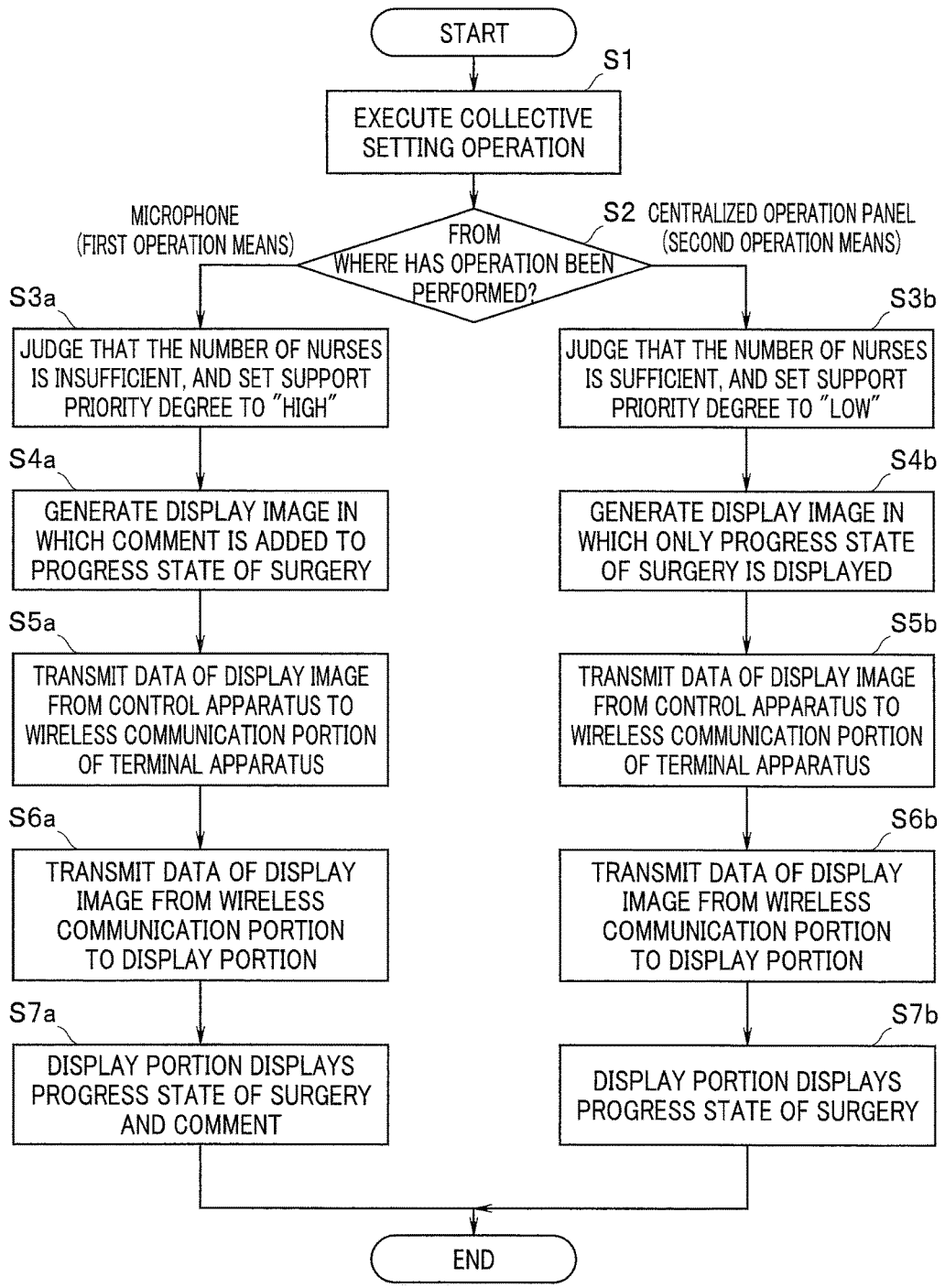

| SURGICAL PROCEDURE PHASE | ENDOSCOPE INSERTION, GALLBLADDER REMOVAL | PREPARATION, SURGICAL INCISION CLOSING |
|---|---|---|
| JUDGMENT ON WHETHER INTRAOPERATIVE PHASE OR NOT | INTRAOPERATIVE PHASE | PHASE OTHER THAN INTRAOPERATIVE PHASE |
| SUPPORT PRIORITY DEGREE | HIGH | LOW |
| DISPLAY COMMENT | A SURGERY IS BEING PERFORMED. YOUR SUPPORT IS REQUESTED. | — |

MEDICAL SYSTEM

CROSS REFERENCE TO RELATED APPLICATION

This application is a continuation application of PCT/JP2014/077511 filed on Oct. 16, 2014 and claims benefit of Japanese Application No. 2013-256209 filed in Japan on Dec. 11, 2013, the entire contents of which are incorporated herein by this reference.

BACKGROUND OF THE INVENTION

1. Field of the Invention

The present invention relates to a medical system for performing surgery using an endoscope.

2. Description of the Related Art

Recently, endoscopes have been widely used in surgeries and the like. In an endoscopic surgery in which surgery is performed under observation with an endoscope, an incision part is small in comparison with a laparotomy surgery, and quick recovery is expected. Therefore, the endoscopic surgery has continued to spread as a surgery method with a small burden on a patient especially since the 1990s.

In the endoscopic surgery described above, a surgeon, and a plurality of assistants, scrub nurses and circulating nurses are disposed.

Conventionally, at least one circulating nurse is arranged in one operating room. However, with increase in the number of surgeries, such cases that a plurality of circulating nurses are responsible for a plurality of operating rooms have been increasing. In general, the circulating nurse directly goes to operating rooms and decides which operating room to enter to give support by confirming progress states of surgeries.

As a technique making it possible to confirm a progress state in an operating room without directly going to the operating room, for example, Japanese Patent Application Laid-Open Publication No. 2011-50653 as a first prior-art example discloses a notification apparatus provided with detection means configured to electrically detect progress of a surgery and notification means configured to notify the detected progress to an outside of the operating room.

Further Japanese Patent Application Laid-Open Publication No. 2012-053750 as a second prior-art example discloses a notification apparatus which detects power consumption in an operating room and distributes a progress state of a surgery to an outside of the operating room based on the detected power consumption.

SUMMARY OF THE INVENTION

A medical system according to an aspect of the present invention includes: a plurality of medical apparatuses used for surgery using an endoscope; a communication-with-apparatus portion configured to communicate with the plurality of medical apparatuses; a replacement portion configured to replace operation setting values for causing the plurality of medical apparatuses to operate along a procedure for the surgery with progress state information indicating progress of the surgery; a priority degree setting portion configured to set a support priority degree for adding information about necessity of a nurse to support the surgery as information about the support priority for smoothly advancing the surgery, to the progress state information; a first operation setting portion configured to be capable of operating the operation setting values of the medical apparatuses from a sterile area; a second operation setting portion configured to be capable of operating the operation setting values of the medical apparatuses from a non-sterile area where the plurality of medical apparatuses are arranged; a transmission portion configured to transmit the progress state information; a control apparatus including the communication-with-apparatus portion, the replacement portion, the priority degree setting portion and the transmission portion; and a terminal apparatus including: a receiving portion configured to receive the progress state information transmitted from the transmission portion; and a display portion configured to display the progress state information received by the receiving portion; wherein the priority degree setting portion includes a judgment portion configured to judge that the support priority degree is high when the operation setting values of the medical apparatuses are operated from the first operation setting portion in comparison with time of the operation setting values being operated from the second operation setting portion, and the priority degree setting portion sends information about the support priority degree corresponding to a case where the support priority degree is judged to be high by the judgment portion, to the transmission portion to add the information about the necessity of the nurse to support the surgery as the information about the support priority degree to the progress state information; and the display portion of the terminal apparatus displays the information about the support priority degree together with the progress state information received by the receiving portion.

BRIEF DESCRIPTION OF THE DRAWINGS

FIG. 4B is a diagram showing scene items along the surgical procedure and states of operation setting values of the plurality of medical apparatuses for each scene item in a tabular format;

FIG. 5 is a diagram showing judgment results of support priority degrees and the like set corresponding to first and second operation means;

FIG. 6 is a diagram showing an example of data used for generation of a display image;

FIG. 8A is a flowchart showing operation content in the first embodiment;

DETAILED DESCRIPTION OF THE PREFERRED EMBODIMENTS

Embodiments of the present invention will be described below with reference to drawings.
(First Embodiment)

Figure 1:
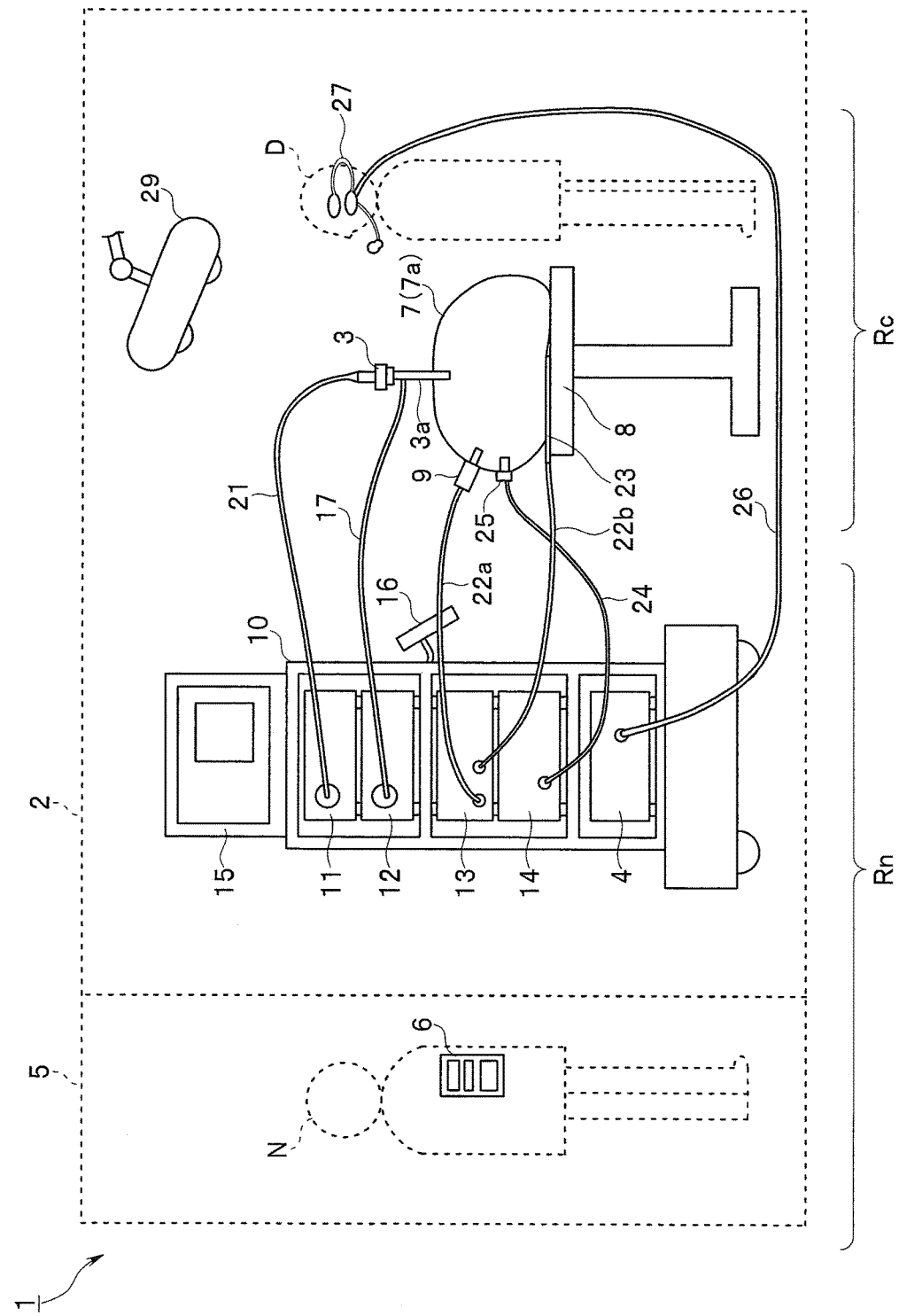
FIG. 1 is a configuration diagram showing a whole medical system of a first embodiment of the present invention.
Figure 13:
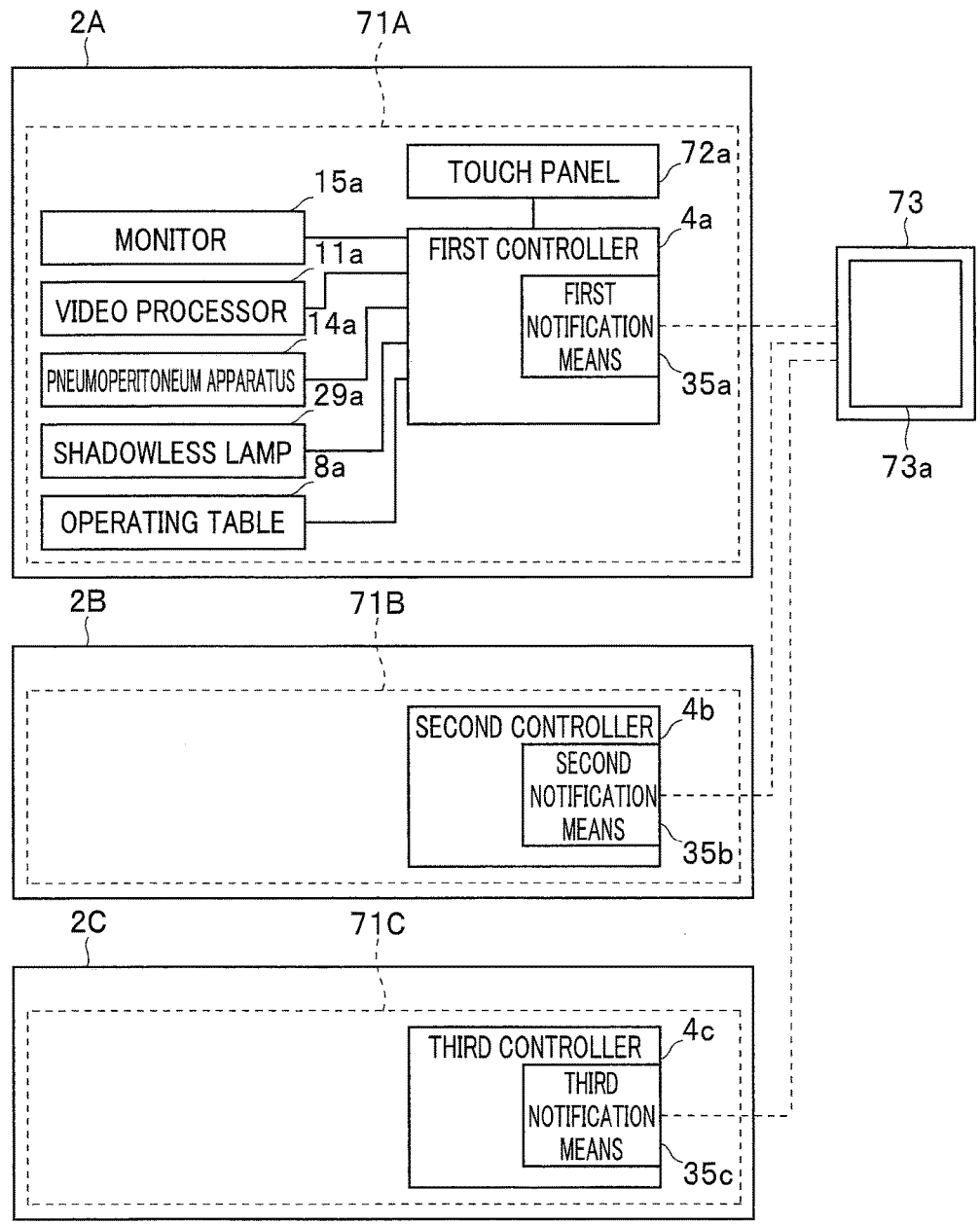
FIG. 13 is a diagram showing a whole configuration of a medical system different from the medical systems of the first and second embodiments.

As shown in FIG. 1, a medical system 1 of a first embodiment of the present invention is provided with: an endoscope 3 arranged in an operating room 2, a control apparatus 4, a plurality of medical apparatuses controlled by the control apparatus 4, and a terminal apparatus 6 carried by a circulating nurse who is disposed being movable within a non-sterile area Rn, including an area 5 outside the operating room 2, and supports surgeries in the operating room 2 (and other operating rooms) (hereinafter abbreviated simply as a nurse) N. Note that, though FIG. 1 shows only one operating room 2, the present embodiment is applicable to a case of a plurality of operating rooms 2A, 2B and 2C (as shown in FIG. 13). Medical systems having a configuration similar to that shown in FIG. 1 are arranged in the other operating rooms, and surgeries are performed. Further, though FIG. 1 shows the single terminal apparatus 6 and the single nurse N, the present embodiment is applicable to a case of a plurality of terminal apparatuses and a plurality of nurses.

In the operating room 2, an operating table 8 on which a patient 7 is placed is arranged. Near the operating table 8, a surgeon D who performs surgery using, for example, an electrode for electric knife (hereinafter referred to simply as an electrode) 9 as a treatment instrument under observation by the endoscope 3 is arranged.

Note that a sterile area Rc as a sterilized clean area is formed in an area surrounding the operating table 8. Apart from the sterile area Rc, a movable trolley 10 is arranged in the non-sterile area Rn as a non-sterilized area. A video processor 11, a light source apparatus 12, an electric knife apparatus 13, a pneumoperitoneum apparatus 14 and a monitor 15 as the plurality of medical apparatuses as controlled apparatuses which are controlled by the control apparatus 4 are mounted on the trolley 10 together with the control apparatus 4. The control apparatus 4 also controls operation (on/off) of a shadowless lamp 29 as one of the plurality of medical apparatuses, which is to be described later.

Further, a centralized operation panel 16 making it possible to perform centralized operations is attached to a side of the trolley 10. The centralized operation panel 16 is configured having a display portion (or display apparatus) 16a (see FIG. 2), for example, configured with a liquid crystal display and a touch panel 16b integrally provided on the display portion 16a. The centralized operation panel 16 is a centralized operation apparatus making it possible for the nurse N in the non-sterile area Rn (who is in a state of being absent from the operating room 2 in FIG. 1) to touch the touch panel 16b to perform an operation of setting operations for the plurality of medical apparatuses. Further, the surgeon D can observe an operation screen displayed on the display portion 16a of the centralized operation panel 16 and can operate the centralized operation panel 16 by voice input as described later.

Note that the surgeon D in the sterile area Rc can also perform an operation by voice through a microphone 27, which is to be described later, while watching a display screen of the display portion 16a.

The light source apparatus 12 includes a light source such as a lamp and transmits (or supplies) illuminating light generated by the light source to the endoscope 3 via a light guide cable 17. The illuminating light transmitted through the light guide cable 17 is emitted from an illuminating window 19a (see FIG. 2) of a distal end portion of an insertion portion 3a of the endoscope 3 via a light guide 18 inside the endoscope 3. Note that the insertion portion 3a of the endoscope 3 is inserted into an abdomen 7a of the patient 7 via a trocar not shown.

At the distal end portion of the insertion portion 3a, an observation window 19b is provided adjacently to the illuminating window 19a, and an image pickup portion (or image pickup device) 20 (see FIG. 2) configured to pick up an image of an object such as a lesion illuminated by illuminating light is provided. The image pickup portion 20 is configured with an objective lens 20a configured to form an optical image of the object and an image pickup element 20b such as a charge coupled device arranged at an image forming position of the objective lens 20a. The image pickup portion 20 is connected to the video processor 11 which forms a signal processing apparatus, via a cable in the endoscope 3 and a video cable 21 extended from the endoscope 3.

The video processor 11 performs signal processing for the image pickup element 20b to generate a video signal (image signal) and outputs the video signal to the monitor 15 as a display apparatus. Then, the monitor 15 displays an image picked up by the image pickup portion 20 on a display surface as an endoscopic image.

The electric knife apparatus 13 which forms an electrical energy supply apparatus is inserted into the abdomen 7a via an electric knife cable 22a and supplies a high-frequency current which forms high-frequency electrical energy, to the electrode 9 as a treatment instrument for performing treatment. Further, a counter electrode or patient plate 23 arranged in a manner of being in contact with a wide area of an outer surface of the patient 7 returns the high-frequency current which has flowed through the patient 7 to the electric knife apparatus 13 via a return cable 22b.

Note that, in a case of using a bipolar electrode, a bipolar electrode cable is connected to the electric knife apparatus 13.

The pneumoperitoneum apparatus 14 is connected to a trocar 25 to be inserted into the abdomen 7a via a pneumoperitoneum tube 24. The pneumoperitoneum apparatus 14 supplies gas for pneumoperitoneum to a trocar 25 side via the pneumoperitoneum tube 24 to perform pneumoperitoneum so as to inflate an inside of the abdomen 7a so that a field of view for observation by the endoscope 3 is secured, and space for performing treatment with the electrode 9 is generated.

The control apparatus 4 is connected to a head-set type microphone (abbreviated simply as a microphone) 27 as a voice input device forming first operation means (or a first operation portion) for performing an operation from the sterile area Rc, which is put on a head portion of the surgeon D in the sterile area Rc via microphone cable 26. Note that the microphone 27 may be configured having an earphone. By inputting voice from the microphone 27, the surgeon D in the sterile area Rc can set operation setting values for causing the plurality of medical apparatuses arranged in the non-sterile area Rn to operate, for example, using display on the display portion 16a of the centralized operation panel 16.

In comparison, the centralized operation panel 16 arranged in the non-sterile area Rn forms second operation means (or second operation portion) configured for the nurse N in the non-sterile area Rn to operate (specifically, touch-operate) the plurality of medical apparatuses from the non-sterile area Rn. Note that the surgeon D or the nurse N sets the operation setting values for causing the plurality of medical apparatuses to operate, for each of procedure phase items (also referred to as scene items) along a surgical procedure, and the set plurality of operation setting values (for causing the medical apparatuses to operate) are stored in a storage portion 31a (see FIG. 2) configured with a storage device inside the control apparatus 4. Therefore, the storage portion 31a forms an operation setting value storing portion or an operation setting value storing device configured to store the operation setting values of the plurality of medical apparatuses.

By setting each of the operation setting values of the plurality of medical apparatuses stored in the storage portion 31a for each of the corresponding plurality of medical apparatuses, operations of the plurality of medical apparatuses are set. In this case, a system control portion 31 sets each of the operation setting values of the plurality of medical apparatuses stored in the storage portion 31a for each of the corresponding plurality of medical apparatuses via an communication-with-apparatus portion 32.

Further, the system control portion 31 performs control operation for collectively setting the operation setting values of the plurality of medical apparatuses in response to a collective setting instruction operation from (a touch operation portion of) the centralized operation panel 16 or the microphone 27.

Thus, (the touch operation portion of) the centralized operation panel 16 and the microphone 27 constitute a collective setting portion (or a collective setting device) as collective setting means configured to collectively set settings for the plurality of medical apparatuses. Note that it is possible to define what includes the communication-with-apparatus portion 32 forms the collective setting portion, in addition to (the touch operation portion) of the centralized operation panel 16 or the microphone 27.

Further, as described later, the control apparatus 4 is provided with a function of an operation portion identifying portion (or operation portion identifying circuit) 31d configured to identify which operation means (or operation portion) between the centralized operation panel 16 and the microphone a collective setting operation has been performed from.

The shadowless lamp 29 is arranged near a position above the operating table 8 on a ceiling of the operating room 2 and performs illumination to brightly illuminate a vicinity of the abdomen 7a of the patient 7 so that the surgeon D can easily perform surgery and the like. The control apparatus 4 controls on/off of lighting operation of the shadowless lamp 29.

Figure 2:
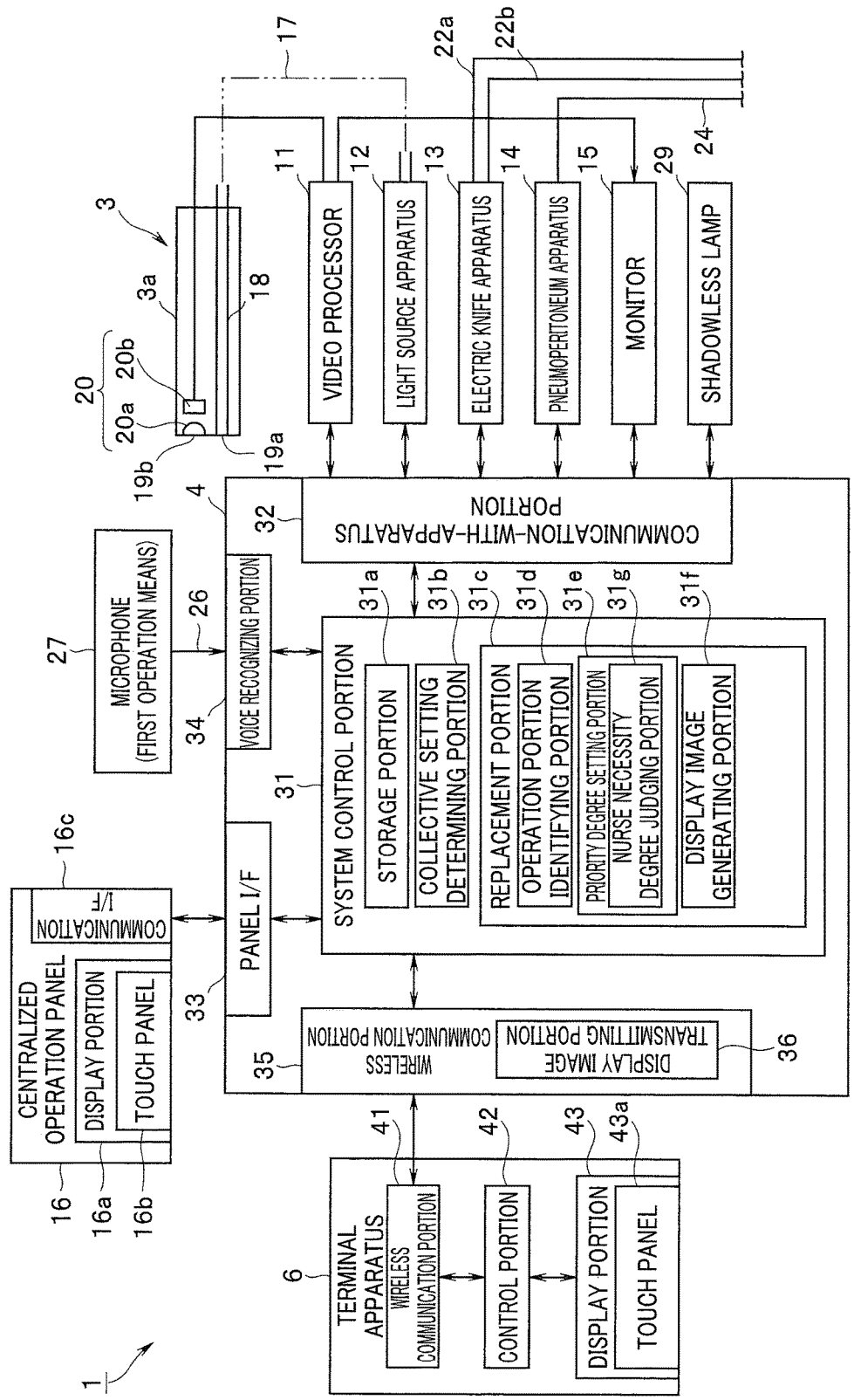
FIG. 2 is a diagram showing internal configurations of a control apparatus and the like in the medical system of FIG. 1.

FIG. 2 shows internal configurations of the control apparatus 4 and the like in the medical system 1 of FIG. 1. As shown in FIG. 2, the control apparatus 4 has: the system control portion (or system control circuit) 31 configured, for example, with a central processing unit (abbreviated as a CPU) configured to control the plurality of medical apparatuses and the like; the communication-with-apparatus portion (or communication-with-apparatus circuit) 32 which forms communication-with-apparatus means configured to communicate with the plurality of medical apparatuses; a panel interface (panel I/F) 33 as an interface to the centralized operation panel 16; a voice recognizing portion (voice recognizing circuit) 34 configured to perform voice recognition of a voice input of the microphone 27; and a wireless communication portion for terminal (or wireless communication circuit for terminal; abbreviated simply as a wireless communication portion) 35 configured to perform wireless communication with the terminal apparatus 6.

As shown in FIG. 2, the system control portion 31 wiredly or wirelessly communicates with the video processor 11, the light source apparatus 12, the electric knife apparatus 13, the pneumoperitoneum apparatus 14, the monitor 15 and the shadowless lamp 29 as the plurality of medical apparatuses via the communication-with-apparatus portion 32 provided with communication interfaces such as a wired RS-232C interface and a wireless communication interface, and controls the operation setting values (or content of setting of operations) including on/off of operation of each medical apparatus.

The wireless communication portion 35 provided with the wireless communication interface has a function of a display image transmitting portion (or display image transmitting circuit) 36 configured to transmit an image for display (also referred to as a display image) including information about a progress state of a surgery, to a display portion (or display device) 43 of the terminal apparatus 6. Thus, the display image transmitting portion 36 has a function of a transmission portion (or transmission circuit) configured to transmit the information about the progress state of the surgery.

The system control portion 31 has: the storage portion 31a configured with a storage device such as a flash memory, which is configured to store the operation setting values for causing the plurality of medical apparatuses to operate (including a setting value of OFF for preventing operation) along a procedure for surgery performed under observation with the endoscope 3, using the endoscope 3; a collective setting determining portion (or collective setting determining circuit) 31b configured to determine collective setting for the plurality of medical apparatuses using the operation setting values read out from the storage portion 31a and determine execution; and a replacement portion (or replacement circuit) 31c as replacement means configured to replace (perform a process for replacing) the operation setting values of the plurality of medical apparatuses set by the collective setting determining portion 31b or the collective setting portion described above with information about a progress state (or progress stage) indicating progress of a surgery.

The operation setting values for causing the plurality of medical apparatuses to operate, which are set by the surgeon D or the nurse N as described above, are associated with a plurality of scene items for which different operation setting items are set for the plurality of medical apparatuses along a surgical procedure and stored in the storage portion 31a, for example, in a lookup table (abbreviated as LUT) format. For example, as shown in FIG. 4B, the storage portion 31a stores the operation setting values for causing the plurality of medical apparatuses to operate in association with a plurality of scene items along a surgical procedure, for example, in an LUT format. As described later, the plurality of scene items along the surgical procedure temporally sequentially form progress states information about a surgery.

The collective setting determining portion 31b described above makes a determination (confirmation) so that the plurality of medical apparatuses for which the operation setting values are collectively set, respectively, by the collecting setting portion to be executed (operated) with the operation setting values, in response to a collective setting operation by the collecting setting portion configured with the microphone 27 described above. Therefore, the collective setting determining portion 31b confirms the collective setting operation of the collective setting portion described above, and, after the confirmation, the system control portion 31 performs control so as to cause the plurality of medical apparatuses to operate with their respective operation setting values through the communication-with-apparatus portion 32.

Note that, though the example shown in FIG. 2 adopts a configuration in which the control apparatus 4 is provided with the collective setting determining portion 31b, such a configuration is also possible that the centralized operation panel 16 has a function of the collective setting determining portion 31b.

Further, the replacement portion 31c has: an operation portion identifying portion (or operation portion identifying circuit) 31d configured with a judgment circuit or the like configured to identify (or judge) which operation portion (operation means) between the centralized operation panel 16 and the microphone 27 settings for the plurality of medical apparatuses have been made from; a priority degree setting portion (or priority degree setting circuit) 31e configured with a comparison circuit or the like configured to set (or judge) a support priority degree (or support level) as support information for giving support so that surgery can be smoothly performed, based a result of the identification by the operation portion identifying portion 31d; and a display image generating portion (or display image generating circuit) 31f configured with an image generating circuit or the like configured to generate a display image to be displayed on the display portion 43 on a terminal apparatus 6 side.

In a case of generating the display image to be displayed on the display portion 43 of the terminal apparatus 6, the display image generating portion 31f may generate a part of the display image while a control portion 42 of the terminal apparatus 6 generating the remaining part, or the display image generating portion 31f may generate only data to be a basis of the display image.

Note that, though the configuration example shown in FIG. 2 shows that the replacement portion 31c is configured having the operation portion identifying portion 31d, the priority degree setting portion 31e and the display image generating portion 31f, a configuration is also possible in which one, two or three among the operation portion identifying portion 31d, the priority degree setting portion 31e and the display image generating portion 31f are provided outside the replacement portion 31c.

Further, a configuration is also possible in which the replacement portion 31c includes the storage portion 31a. When the collective setting determining portion 31b confirms a collective setting operation by the collecting setting portion, the replacement portion 31c replaces collectively set operation setting values of the plurality of medical apparatuses with corresponding surgery progress state information by referring to the LUT in the storage portion 31a and identifying the collectively set operation setting values of the plurality of medical apparatuses as corresponding scene items. Thus, the replacement portion 31c can be configured with a readout circuit configured to read out, from one piece of information in an LUT, the other corresponding piece of information and output the read-out information.

The priority degree setting portion 31e has a function of a nurse necessity degree judging portion (or nurse necessity degree judging circuit) 31g configured with a comparison circuit or the like configured to make a judgment on a degree of necessity of (support by) a supporting nurse as the support priority degree.

The centralized operation panel 16 is provided with a communication interface (communication I/F) 16c configured to perform communication with the panel interface 33, and the display portion 16a and the touch panel 16b which have been described above.

The terminal apparatus 6 has: a wireless communication portion (or wireless communication circuit) 41 configured to perform wireless communication with the wireless communication portion 35; the control portion (or control circuit) 42 configured to control operation of the whole terminal apparatus 6; and the display portion (or display device) 43 configured to display a display image generated by the display image generating portion 31f of the control apparatus 4 by communicating with the control apparatus 4.

The wireless communication portion 41 has a function of a receiving portion (or receiving circuit) configured to receive at least the progress state information transmitted from a wireless communication portion 35 side by performing wireless communication with the wireless communication portion 35.

Further, the wireless communication portion 41 has a function of a receiving portion (or receiving circuit) configured to, when such information that support priority degree information is added to progress state information is transmitted from the wireless communication portion 35 side, receive the progress state information and the support priority degree information.

The display portion 43 is formed, for example, by a liquid crystal display, and a touch panel 43a is integrally provided on the display portion 43.

The control portion 42 receives display image data (also referred to simply as a display image) including at least the progress state information, transmitted from a control apparatus 4 side and displays the display image data as in FIG. 7 as described later, on the display portion 43 in which the touch panel 43a is formed, and displays an operation screen for accepting a touch operation on the touch panel 43a.

The nurse N carrying the terminal apparatus 6 can perform a touch operation on the touch panel 43a to transmit a reply signal or the like to the effect that the nurse N has confirmed the transmitted display image, from the wireless communication portion 41 to the wireless communication portion 35 of the control apparatus 4.

Further, when making the reply, the terminal apparatus 6 can also add and transmit character information such as a comment. Note that, when the reply signal is returned from the terminal apparatus 6 side, the control apparatus 4 may judge whether content of the reply signal is such that a support priority degree transmitted before receiving the reply signal is to be changed or not, and change the support priority degree depending on a result of the judgment (to be described later with reference to FIG. 8B).

Figure 3:
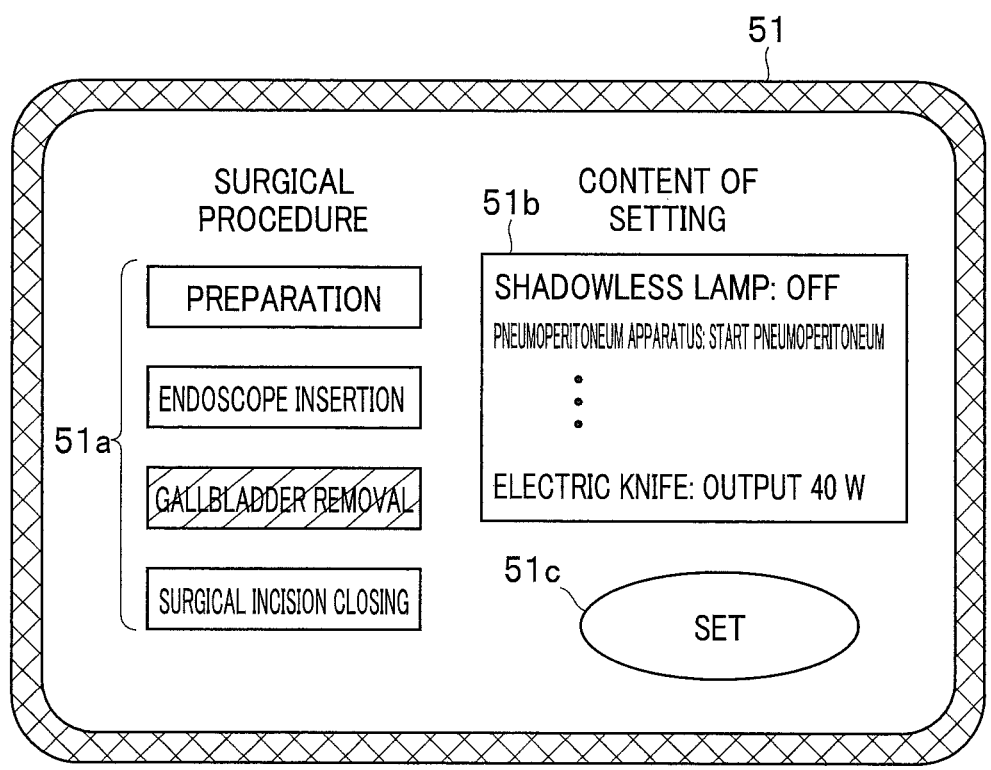
FIG. 3 is a diagram showing an example of a collective setting operation screen on a centralized operation panel for collectively setting operation settings for a plurality of medical apparatuses.

FIG. 3 shows a collective setting operation screen 51 in a case of collectively setting operation setting values of the plurality of medical apparatuses at time of performing surgery, using the display portion 16a of the centralized operation panel 16.

The collective setting operation screen 51 is configured so that a collective setting operation item area 51a for displaying procedure phase items (scene items) classified along a surgical procedure, a setting content display area 51b for displaying setting content of the operation setting values of the respective medical apparatuses, and a set button 51c for making a setting for determining a collecting setting operation are displayed.

The setting content display area 51b has a function of a setting content confirmation area for the nurse N as a user who performs a touch operation in the non-sterile area Rn or the surgeon D as a user who makes a voice input in the sterile area Rc to confirm the operation setting values of the plurality of medical apparatuses.

The plurality of scene items classified along the surgical procedure in the collective setting operation item area 51a are stored in the storage portion 31a, for example, in an LUT format, being associated with combinations of different operation setting values of the plurality of medical apparatuses, respectively, as shown in FIG. 4B. The centralized operation panel 16 reads out the LUT from the storage portion 31a and displays the LUT on the collective setting operation screen 51. When operation setting values of the plurality of medical apparatuses are selected, a scene item corresponding to the selection is determined On the contrary, a scene item is selected, corresponding operation setting values of the plurality of medical apparatuses are determined.

Further, each of the plurality of scene items classified along the surgical procedure corresponds to progress state information about the surgery. That is, the surgery temporally sequentially progresses in the surgical procedure along the plurality of scene items in the collective setting operation item area 51a of FIG. 3, and one scene item to be progress state information sequentially changes along the progress.

By making a selection of operation setting values of the plurality of medical apparatuses (collective setting) or a selection of a scene item via the touch panel 16b on the collective setting operation screen 51 in FIG. 3, (a scene item to be) corresponding progress state information about the surgery is determined from the operation setting values of the plurality of medical apparatuses. In other words, the replacement portion 31c can be regarded as replacing the operation setting values of the plurality of medical apparatuses with the progress state information about the surgery in response to a signal by the touch panel 16b. Note that a signal in the case of touch-operating the touch panel 16b and a signal in the case of operating the touch panel 16b by voice are inputted to (the operation portion identifying portion 31d of) the replacement portion 31c, and the operation portion identifying portion 31d identifies (or judges) which signal a signal is.

Though description will be made on a case of a surgery of, for example, removing a gallbladder in the present embodiment, the present embodiment is applicable to surgery other than gallbladder removal.

Figure 4A:
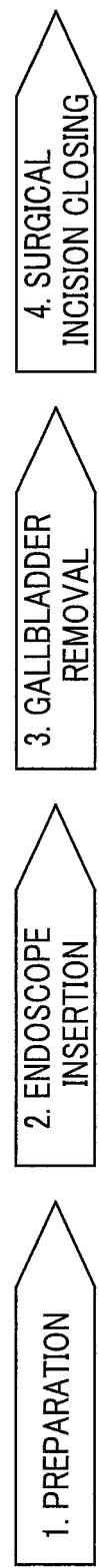
FIG. 4A is a diagram showing an example of a surgical procedure.

In the case of the surgery of removing a gallbladder, scene items along a surgical procedure are "preparation", "endoscope insertion", "gallbladder removal" and "surgical incision closing" as shown in FIG. 3, and the operation is performed in order of 1. preparation, 2. endoscope insertion, 3. gallbladder removal and 4. surgical incision closing as shown in FIG. 4A, which includes the above order.

"Preparation" is a scene item of performing anesthesia and the like for performing surgery using the endoscope 3. "Endoscope insertion" is a scene item of inserting the endoscope 3 in order to observe a surgical site by the endoscope 3. "Gallbladder removal" is a scene item of removing the gallbladder using a treatment instrument under observation with the endoscope 3. "Surgical incision closing" is a scene item of performing suturing in order to end the surgery.

Further, for each of the scene items of "preparation", "endoscope insertion", "gallbladder removal" and "surgical incision closing", the plurality of medical apparatuses are set to operation setting values (operation setting states) corresponding to the scene item as shown in FIG. 4B. For example, for the scene item of "preparation", the shadowless lamp 29 is set to lighting OFF; the pneumoperitoneum apparatus 14 is set to stop pneumoperitoneum; the video processor 11 is set to ON (power source ON); the light source apparatus 12 is set to light source OFF; the monitor 15 is set to ON; and the electric knife apparatus 13 is set to output 0 W. Note that, in FIG. 4B, a down arrow indicates that content is same as content above the down arrow (indicates a state that a previous scene item has not changed).

Further, the storage portion 31a stores information about the operation setting values of the plurality of medical apparatuses in association with each scene item shown in FIG. 4B. Further, in addition, the storage portion 31a stores information such as a number of an operating room where the above surgery is performed, and a name of the patient 7 for whom the surgery is performed.

If the nurse N is in the operating room 2, the nurse N performs (setting for) selection of one scene item in the collective setting operation item area 51a on the centralized operation panel 16 by a touch operation according to progress of the surgery in the non-sterile area Rn, and performs an operation for causing the surgery of the scene item to be executed.

The touch panel 16b judges the touch operation and sends a judgment result to the replacement portion 31c, and the replacement portion 31c replaces the touch-operated scene item with progress state information about the surgery. More specifically, by selecting such a scene item that operation setting values of the plurality of medical apparatuses correspond to content of the surgery to be actually performed, from among the plurality of scene items under which operation setting values of the plurality of medical apparatuses are set differently, according to the surgical procedure, the selected scene item becomes the progress state information about the surgery.

In the example of FIG. 3, a scene item selected from among the plurality of scene items by a touch operation is indicated by oblique lines, and it is shown that the scene item of gallbladder removal is selected, and the gallbladder removal scene item becomes the progress state information.

FIG. 3 shows such operation setting values that the shadowless lamp 29 is set to OFF, the pneumoperitoneum apparatus 14 is set to start pneumoperitoneum, . . . , and the electric knife apparatus 13 is set to output 40 W in association with the gallbladder removal scene item.

When the nurse N touches the set button 51c on the screen after confirming the content, an operation signal of the touch is sent to the system control portion 31. The operation of the set button 51c is judged by the collective setting determining portion 31b of the system control portion 31, and the collective setting determining portion 31b determines (or executes) a collective setting operation. By the decision (or execution) of the collective setting operation, the plurality of medical apparatuses enter a state of being executed with their respective operation setting values. Note that a configuration is also possible in which, after the decision (or execution) of the collective setting operation, an operation of causing the plurality of medical apparatuses to be executed with their respective operation setting values is further required (for confirmation).

Further, in a case where the surgeon D or the like in the sterile area Re performs the collective setting operation using the microphone 27 as first operation means, instead of the nurse the nurse N performing the collective setting operation as described above, the surgeon D also performs the operation by a voice input according to the screen.

In this case, the voice recognizing portion 34 of the control apparatus 4 recognizes an operation signal by the voice input and sends a recognition result to the system control portion 31, and the system control portion 31 performs control so that an operation similar to that in the case of touch-operating the centralized operation panel 16 is performed, according to the recognition result.

Then, by the surgeon D performing a voice input for operating the set button 51c, the collective setting determining portion 31b of the system control portion 31 determines the collective setting operation similarly to the case of the nurse N touch-operating the set button 51c.

When the collective setting operation is determined, the replacement portion 31c replaces the collectively set operation setting values of the plurality of medical apparatuses with progress state information indicating progress of the surgery.

The replacement portion 31c generates the progress state information by referring to information stored in the storage portion 31a (for example, the information in which each scene item is associated with the operation setting values of each of the plurality of medical apparatuses in a LUT format, shown in FIG. 4B, and a first data group 56 of FIG. 6 to be described later). Therefore, the replacement portion 31c can be also referred to as a progress state information generating portion (or progress state information generating circuit) configured to generate progress state information from operation setting values of the plurality of medical apparatuses.

Further, the display image generating portion (display image generating circuit) 31f in the replacement portion 31c generates a display image for displaying the progress state information on the terminal apparatus 6 carried by the nurse N outside the operating room 2, and transmits (the generated display image) via the wireless communication portion 35. The nurse N can grasp the progress state of the surgery in the operating room 2 by watching the display image displayed on the display portion 43 of the terminal apparatus 6.

In the present embodiment, a configuration is adopted in which, in addition to displaying the progress state information as the display image, support priority degree information as information about a degree of necessity about whether support by the nurse N is required or not (that is, a degree of necessity of a nurse) is also added to the progress state information and transmitted to the terminal apparatus 6 for the nurse N. Therefore, the nurse N can easily grasp whether or not to go to the operating room 2 to provide support, by referring to the support priority degree information.

In order to make it possible to transmit the support priority degree information to the terminal apparatus 6 as described above, the operation portion identifying portion 31d identifies (judges) whether an operation of the set button 51c in a collective setting operation has been performed from the microphone 27 as the first operation means or by a touch operation on the centralized operation panel 16 as the second operation means as shown in FIG. 5. Then, the operation portion identifying portion 31d sends an identification (judgment) result to the priority degree setting portion 31e. The operation portion identifying portion 31d sends an identification signal (judgment signal) of the identification result, for example, with an H level when the collective setting operation has been performed from the microphone 27 and with an L level when the collective setting operation has been performed from the centralized operation panel 16. (The nurse necessity degree judging portion 31g) of the priority degree setting portion 31e generates a signal judging a support priority degree from the identification signal which is an input signal, using a comparison circuit in which a threshold level is set between the L level and the H level.

Note that FIG. 5 shows judgment results and the like, such as the support priority degree, by the priority degree setting portion 31e in a tabular format.

(The nurse necessity degree judging portion 31g of) The priority degree setting portion 31e judges the necessity of a nurse as the support priority degree using a comparison circuit or the like according to the judgment results (comparison results).

Specifically, when an operation of the set button 51c in a collective setting operation has been performed by the microphone 27 from the surgeon D of the sterile area Rc, the nurse necessity degree judging portion 31g judges that necessity of the nurse N is high in the surgery. In other words, the nurse necessity degree judging portion 31g judges that the number of nurses is insufficient or that the support priority degree is high and, further adds a comment or a display comment of "The number of nurses is insufficient. Your support is requested." Thus, (the nurse necessity degree judging portion 31g of) the priority degree setting portion 31e further has a function of a character information generating portion (or character information generating circuit) configured to generate character information for a comment forming support priority degree information corresponding to a support priority degree judgment result.

Note that, though the display comment is registered with the storage portion 31a or the priority degree setting portion 31e in advance so as to be added at least in a case where the support priority degree is high, it is also conceivable that the display comment can be added with use of the centralized operation panel 16.

On the other hand, when the operation of the set button 51c in the collective setting operation has been performed by a touch operation on the centralized operation panel 16 from the nurse N in the non-sterile area Rn, the nurse necessity degree judging portion 31g judges that the necessity of a nurse is low in the surgery, in other words, that there is a sufficient number of nurses, and judges that the support priority degree is low. In this case, for example, the display comment is not added.

Note that, though the support priority degree information may be defined as "high" and "low", to be information corresponding to judgment results of the support priority degree, a display comment (corresponding to judgment result information) may be defined as the support priority degree information. To supplementarily make a description, when only "high" or "low" is displayed, which corresponds to (a judgment result of) the support priority degree, as the support priority degree information on the terminal apparatus 6, the nurse N watching the terminal apparatus 6 can roughly grasp its meaning. However, if the display comment of "The number of nurses is insufficient. Your support is requested" is further added and displayed when it is displayed that the support priority degree is "high" or "low", the nurse N can more easily grasp its meaning and can more easily start an action of support.

Further, by preventing the support priority degree information from being displayed when the support priority degree is "low", the nurse N can easily grasp that the nurse N is not required. In this case, it is also possible to display "There is a sufficient number of nurses" as a comment to more clarify that support is not required. In this way, it is possible to, when the support priority degree is high, transmit and display the support priority degree information, and, when the support priority degree is low, transmit and display the support priority degree information or prevent the support priority degree information from being transmitted (displayed).

The priority degree setting portion 31e sends the support priority degree information to the display image generating portion 31f according to a support priority degree judgment result. The display image generating portion 31f adds the support priority degree information to the progress state information to generate a display image. FIG. 6 shows an example of data used for generation of a display image. FIG. 6 shows data used for generation of a display image in a state in which the support priority degree is high when an operation is performed by the microphone 27 in FIG. 5.

As data items used for generation of a display image, a first data group (or first data item group) 56 for displaying an operating room No. (as number information identifying an operating room) and patient information, a second data group (or second data item group) 57 for displaying a progress state of a surgery, and a third data group (or third data item group) 58 for displaying a support priority degree and a display comment. The display image generating portion 31f generates a display image from these data groups 56 to 58 and transmits the display image from the wireless communication portion 35 to the terminal apparatus 6. In addition to support priority degree information, the operating room No., the patient information and the like for which the support priority degree information is generated are added to the progress information (in FIG. 6, information about gallbladder removal) and transmitted from the wireless communication portion 35 to the terminal apparatus 6. Note that, the operating room No. and the patient information are inputted to the control apparatus 4 from the centralized operation panel 16 or the like when a surgery is started in each operating room, and the storage portion 31a stores the inputted information.

The wireless communication portion 41 of the terminal apparatus 6 displays the received display image on the display portion 43. Note that the priority degree setting portion 31e may wirelessly communicate (wirelessly transmit) the display image to which the priority degree information and the like are added, to the terminal apparatus 6 via the wireless communication portion 35.

Figure 7:
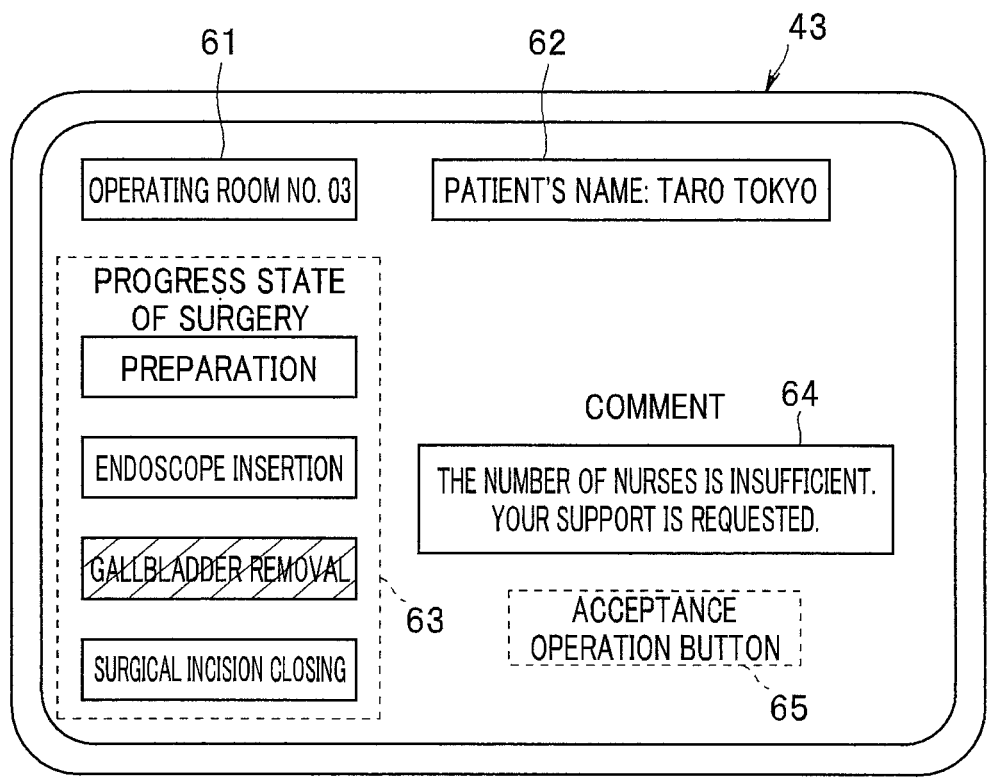
FIG. 7 is a diagram showing an example of the display screen displayed on a terminal apparatus.

FIG. 7 shows an example of a display screen displayed on the display portion 43 of the terminal apparatus 6 in a case of the data of FIG. 6.

The display screen of the display portion 43 of the terminal apparatus 6 is provided with: a first display area 61 for displaying No. of the operating room 2, a second display area 62 for displaying a patient name, and a third display area 63 for displaying progress state information about a surgery by displaying a scene item actually being executed (in FIG. 7, indicated by oblique lines) among a plurality of scene items classified along a surgical procedure, and a fourth display area 64 for displaying the support priority degree information or a comment (or a display comment) as more specified information of the support priority degree information.

Further, though the displayed progress state information about the surgery is indicated by changing a display color of the scene item which is being executed to be different from a display color of other scene items which are not being executed (in FIG. 7, the relevant scene item is indicated by oblique lines), other display methods may be adopted. For example, display characters of the relevant scene item may be shown in bold so that the display characters can be easily distinguished from the other scene items.

The display image generating portion 31f generates display image data for terminal apparatus based on the information shown in FIG. 6, and the generated display image data for terminal apparatus is sent to the terminal apparatus 6 via the wireless communication portion 35 and the wireless communication portion 41 and displayed on the display portion 43 of the terminal apparatus 6 as shown in FIG. 7.

The medical system 1 of the present embodiment includes: the plurality of medical apparatuses used in surgery using the endoscope 3, such as the video processor 11, the light source apparatus 12, the electric knife apparatus 13, the pneumoperitoneum apparatus 14, the monitor 15 and the shadowless lamp 29; the communication-with-apparatus portion 32 configured to communicate with the plurality of medical apparatuses; the storage portion 31a configured to store operation setting values for causing the plurality of medical apparatuses to operate along a procedure for the surgery; the microphone 27 as the first operation means and the centralized operation panel 16 as the second operation means constituting the collective setting portion configured to collectively set settings for the plurality of medical apparatuses using the operation setting values stored in the storage portion 31a; the replacement portion 31c configured to replace the operation setting values of the plurality of medical apparatuses collectively set by the collective setting by the collective setting portion with progress state information indicating progress of the surgery; the priority degree setting portion 31e configured to set the support priority degree for adding support priority degree information for smoothly advancing the surgery to the progress state information; the wireless communication portion 35 forming the transmission portion configured to transmit the progress state information; the control apparatus 4 including the communication-with-apparatus portion 32, the storage portion 31a, the replacement portion 31c, the priority degree setting portion 31e and the transmission portion; and the terminal apparatus 6 including the wireless communication portion 41 forming the receiving portion configured to receive the progress state information transmitted from the transmission portion and the display portion 43 configured to display the progress state information received by the receiving portion. The priority degree setting portion 31e sets the support priority degree at an execution timing of causing the plurality of medical apparatuses collectively set by the collective setting portion to be executed with the operation setting values, sends information about the support priority degree to the wireless communication portion 35 forming the transmission portion to add the support priority degree information to the progress state information according to a result of setting of the support priority degree. The display portion 43 of the terminal apparatus 6 displays the support priority degree information together with the progress state information received by the wireless communication portion 41 forming the receiving portion. Note that, as described above, the collective setting portion may be defined as further including the communication-with-apparatus portion 32 configured to set the plurality of operation setting values for the plurality of medical apparatuses through communication. In a case of the definition, the microphone 27 as the first operation means and the centralized operation panel 16 as the second operation means can be regarded as an instruction operation portion (or instruction operation device) configured to perform a collective setting instruction operation.

Next, operation of the present embodiment will be described. FIG. 8A shows a representative example of the operation in a case where a collective setting operation is performed in the present embodiment by a flowchart.

In order that, for example, a gallbladder removal surgery can be performed for the patient 7 as shown in FIG. 1, the surgeon D or the nurse N sets operation setting values of the plurality of medical apparatuses so that the operation setting values suit to the respective scene items of preparation, endoscope insertion, gallbladder removal and surgical incision closing as shown in FIG. 4B.

In the case of performing a gallbladder removal surgery, it is common that the nurse N in the non-sterile area Rn sets the operation setting values of the plurality of medical apparatuses by performing a touch operation on the centralized operation panel 16 if there is a sufficient number of nurses. If there is not a sufficient number of nurses, the surgeon D in the sterile area Rc performs an operation of the centralized operation panel 16 using voice input by the microphone 27 to set the operation setting values of the plurality of medical apparatuses.

In this way, as shown at step S1 in FIG. 8A, the surgeon D or the nurse N performs a collective setting operation for determining collective setting of operation setting values for the plurality of medical apparatuses to cause the plurality of medical apparatuses to be executed (with the respective operation setting values) by an operation of the set button 51c (by a voice input or a touch operation).

When the operation of causing the collective setting operation to be executed is performed, the operation portion identifying portion 31d identifies (judges) which of the microphone 27 as the first operation means in the sterile area Rc and (a touch operation by) the centralized operation panel 16 as the second operation means in the non-sterile area Rn the collective setting operation has been performed, as shown at step S2. Then, the operation portion identifying portion 31d sends a result of the identification (judgment) to the priority degree setting portion 31e.

When operation has been performed from the microphone 27 in the sterile area Rc, the nurse necessity degree judging portion 31g of the priority degree setting portion 31e judges that the number of nurses is insufficient for the surgery and sets the support priority degree to "high" as shown at step S3a. Further, when collective setting of the operation setting values for the plurality of medical apparatuses is determined, corresponding progress state information is generated by the replacement portion 31c.

As shown at next step S4a, the display image generating portion 31f generates a display image in which a comment indicating the support priority degree information more specifically is added to the progress state information about the surgery.

As shown at next step S5a, the control apparatus 4 wirelessly transmits data of the display image generated by the display image generating portion 31f to the wireless communication portion 41 of the terminal apparatus 6 using the wireless communication portion 35.

As shown at next step S6a, the wireless communication portion 41 sends the received display image data to the display portion 43.

As shown at next step S7a, the display portion 43 displays the progress state of the surgery and the comment. The nurse N carrying the terminal apparatus 6 recognizes that support is required by watching the progress state of the surgery and comment displayed on the display portion 43 and goes to the operating room 2 requiring support, so that nurse N can quickly support the surgery in the operating room, and the surgery can be smoothly advanced.

On the other hand, if a touch operation has been performed from the centralized operation panel 16 as the second operation means in the non-sterile area Rn at step S2, the nurse necessity degree judging portion 31g of the priority degree setting portion 31e judges that there is a sufficient number of nurses for the surgery and sets the support priority degree to "low" as shown at step S3b. As shown at next step S4b, the display image generating portion 31f generates a display image on which only the progress state of the surgery is displayed.

As shown at next step S5b, the control apparatus 4 wirelessly transmits data of the display image generated by the display image generating portion 31f to the wireless communication portion 41 of the terminal apparatus 6 using the wireless communication portion 35.

As shown at next step S6b, the wireless communication portion 41 sends the received display image data to the display portion 43.

As shown at next step S7b, the display portion 43 displays the progress state of the surgery. The nurse N carrying the terminal apparatus 6 can grasp the progress state of the surgery by watching the progress state of the surgery displayed on the display portion 43. Further, the nurse N can recognize that support is not required.

According to the present embodiment which operates as described above, it is possible to display the support priority degree information making it possible for the nurse N to easily judge which operating room the nurse N should preferentially go to in order to support surgery in the operating room, on the terminal apparatus 6 carried by the nurse N. Therefore, it is smoothly performed for the nurse N carrying the terminal apparatus 6 to support surgery in an operating room requiring support by a nurse, and it becomes possible to perform the surgery efficiently.

Figure 8B:
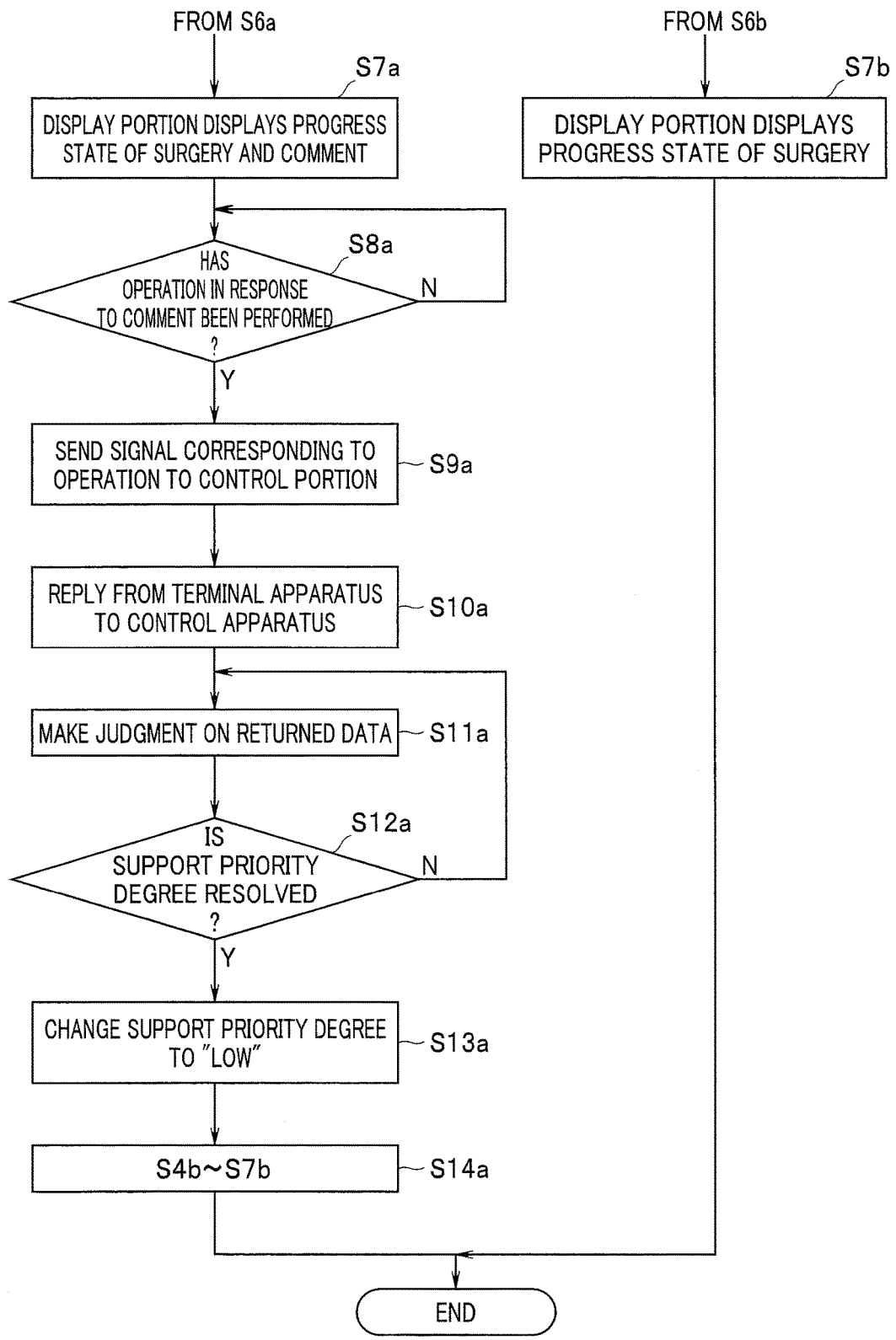
FIG. 8B is a flowchart showing operation content in a case where a process of replying to the operation content of FIG. 8A is performed.

Note that, though it has been described in FIG. 8A that the progress state information and the support priority degree information (comment) are displayed on the display portion 43 of the terminal apparatus 6 so that the nurse N carrying the terminal apparatus 6 can confirm it, a process shown in FIG. 8B may be further performed.

After the process of displaying the progress state of surgery and the support priority degree information (comment) on the display portion 43 of the terminal apparatus 6 at step S7a of FIG. 8A, the control portion 42 of the terminal apparatus 6 waits until an operation (a response operation) to the effect that the nurse N is going to give support (hereinafter referred to as acceptance to give support) is performed by the nurse N from the touch panel 43a in response to the display as shown at next step S8a. Note that, in order to more clarify presence/absence of an operation of accepting to give support, an acceptance operation button 65 for performing an operation of accepting to give support (and making a reply) may be displayed near (in FIG. 7, below) the fourth display area 64 for displaying a comment, on the display portion 43 of the terminal apparatus 6 as indicated by a broken line in FIG. 7.

The acceptance operation button 65 forms an operation button for returning a reply signal, for example, to the priority degree setting portion 31e of the control apparatus 4 in a case where it is better at least to reply when the support priority degree information is displayed on the display portion 43 (more specifically, in such a case that information with a high support priority degree is displayed).

As shown at next step S9a, when the acceptance operation button 65 is pressed, the touch panel 43a sends a signal (data) indicating acceptance to give support to the control portion 42. Note that, even when an operation other than the operation of accepting to give support is performed, the touch panel 43a can send a signal corresponding to the operation to the control portion 42.

At next step S10a, if the acceptance operation button 65 is operated, the control portion 42 of the terminal apparatus 6 transmits (returns) reply data of accepting to give support from the wireless communication portion 41 to the control apparatus 4. Even in a case where an operation other than the operation of the acceptance operation button 65 is performed, a signal corresponding to the operation is transmitted (returned) from the wireless communication portion 41 of the terminal apparatus 6 to the control apparatus 4 as reply data.

At next step S11a, (for example, the priority degree setting portion 31e) of the system control portion 31 in the control apparatus 4 makes a judgment on the returned data. Then, at next step S12a, the priority degree setting portion 31e judges whether the returned data indicates acceptance to give support which resolves the support priority degree. If a judgment result is such that does not resolve the support priority degree, the flow returns to the process of step S11a.

On the other hand, if the judgment result is such that resolves the support priority degree, the flow proceeds to a process of step S13a, and the priority degree setting portion 31e judges that the support priority degree has been resolved and changes the support priority degree from "high" to "low".

In this case, display showing "A reply that a nurse is going to give support has arrived", "Since a reply that a nurse is going to give support has arrived, the supporting nurse will come soon" or the like may be displayed on the display portion 16a of the centralized operation panel 16.

After the process of step S13a, a process of steps S4b to S7b shown in FIG. 8A (in FIG. 8B, shown as step S14a) is performed, and the process of FIG. 8B ends.

By doing this, the advantageous effect of FIG. 8A is obtained, and it becomes possible to perform surgery more efficiently. That is, if a comment with a high support priority degree is displayed together with progress state information on the terminal apparatus 6 carried by the supporting nurse N when support by the nurse N is required in a progress state of a surgery in a certain operating room, it is desired that the nurse N quickly gives support. Therefore, by making a reply to the effect that the nurse N is going to give support from the nurse N side, the state of the insufficient number of nurses is resolved for the surgery in the operating room, and, further, a problem can be quickly resolved that yet another nurse N doubly gives support. Therefore, it becomes possible to, in a case of performing surgeries in a plurality of operating rooms, perform the surgeries efficiently.

Note that, in an environment in which a time period required for the nurse N to go to the operating room 2 is also to be considered, it is also conceivable that display showing "A reply that a nurse is going to give support has arrived", "A nurse who gives support is asked to operate the centralized operation panel to perform an operation of changing the support priority degree when arriving at the operating room" or the like is shown on the display portion 16a of the centralized operation panel 16, and, when a nurse arrives at the operating room, the nurse operates the centralized operation panel 16 to change the support priority degree from "high" to "low". When the support priority degree is changed from "high" to "low", information about the support priority degree is also changed (as described above) according to the changed support priority degree.

Further, in a case of performing the process shown in FIG. 8A also, the nurse may operate the centralized operation panel 16 to change the support priority degree from "high" to "low" when the nurse arrives at an operating room with high a support priority degree. Note that, in a second embodiment described below, a configuration is also possible in which the first embodiment and the second embodiment are combined as described later.

(Second Embodiment)

Figure 9:
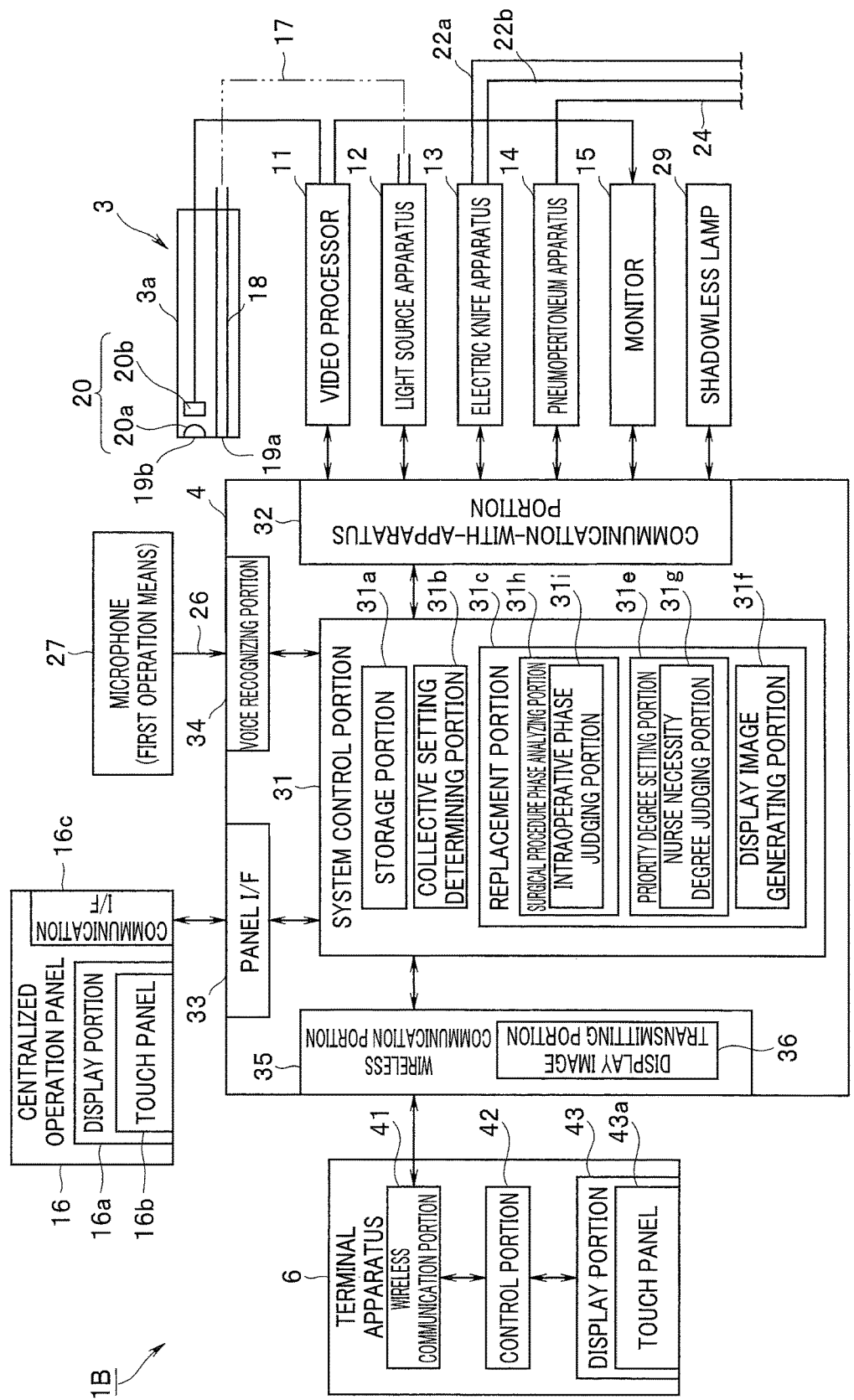
FIG. 9 is a diagram showing a configuration of a medical system of a second embodiment of the present invention.

Next, a second embodiment of the present invention will be described. FIG. 9 shows a medical system 1B of the second embodiment of the present invention. The present embodiment is different from the medical system 1 of FIG. 2 in a configuration of the replacement portion 31c.

The replacement portion 31c in the present embodiment has a surgical procedure phase analyzing portion (or surgical procedure phase analyzing circuit) 31h configured to analyze a surgical procedure phase, instead of the operation portion identifying portion 31d in FIG. 2. Further, the surgical procedure phase analyzing portion 31h has an intraoperative phase judging portion (intraoperative phase judging circuit) or a surgical phase judging portion (surgical phase judging circuit) 31i configured to determine a collective setting operation and judge whether (a scene item of) a surgical procedure phase is an intraoperative phase (or state) or a phase (or state) other than the intraoperative phase (or state) at an execution timing of the plurality of medical apparatuses being automatically executed or an execution timing of an operation of causing the plurality of medical apparatuses to be executed being performed.

The nurse necessity degree judging portion 31g of the priority degree setting portion 31e judges a nurse's support priority degree according to a result of judgment by the intraoperative phase judging portion 31i. The storage portion 31a classifies each of a plurality of scene items associated with operation setting values of the plurality of medical apparatuses according to whether the scene item is an intraoperative scene item indicating that a surgery is substantially performed, or a scene item other than the intraoperative scene item indicating that a surgery is substantially not performed and stores the scene item in advance. More specifically, the storage portion 31a stores the scene items of endoscope insertion and gallbladder removal as information corresponding to the intraoperative phase, and the scene items of preparation and surgical incision closing as information corresponding to the phase other than the intraoperative phase, as described below.

Note that the storage portion 31a may store information in which operation setting values in the case of being collectively set by the collective setting portion and the information about whether a scene item is an intraoperative scene item or not are mutually associated. Further, since the operation setting values in the case of being collectively set by the collective setting portion are replaced with progress state information by the replacement portion 31c, the storage portion 31a may further store the progress state information or may store the progress state information in which the associated information is included.

Figures 10, 11:
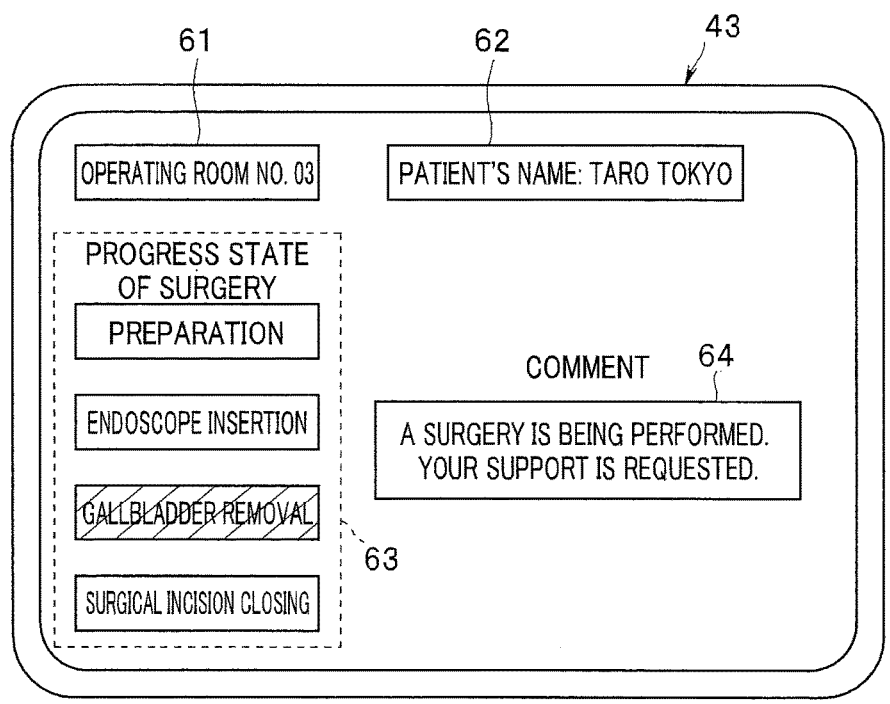
FIG. 10 is a diagram showing support priority degrees and the like corresponding to judgment results of an intraoperative phase judging portion in a tabular format.
FIG. 11 is a diagram showing an example of a display screen displayed on a display portion of the terminal apparatus.

FIG. 10 shows judgment results of the intraoperative phase judging portion 31i, corresponding support priority degrees and the like in the case of the present embodiment.

The intraoperative phase judging portion 31i judges which phase a surgical procedure phase at the time of performing a collective setting operation corresponds to, among endoscope insertion and gallbladder removal, which are intraoperative phases, and preparation and surgical incision closing, which are phases other than the intraoperative phases.

Note that, as for whether the phase is the intraoperative phase or not, it is possible to judge that the phase is the intraoperative phase if at least one of the operation setting values (see FIG. 4B) of the light source apparatus 12, the pneumoperitoneum apparatus 14 and the electric knife apparatus 13 which forms an electrical energy supply apparatus, among the plurality of medical apparatuses, is set to an operating state and judge that the phase is not the intraoperative phase if all of the operation setting values are OFF or in an operation stop state corresponding to OFF. In FIG. 4B, the light source apparatus 12 and the pneumoperitoneum apparatus 14 are set to the operating state for the scene item of endoscope insertion, and the light source apparatus 12, the pneumoperitoneum apparatus 14 and the electric knife apparatus 13 are set to the operating state for the scene item of gallbladder removal. In comparison, for the scene items of preparation and surgical incision closing, each of the operation states (operation setting values) is set to the state corresponding to OFF.

In the case of endoscope insertion or gallbladder removal to be the intraoperative phase, the nurse necessity degree judging portion 31g of the priority degree setting portion 31e judges the support priority degree as "high" and adds the comment of "A surgery is being performed. Your support is requested." Since, at the intraoperative phase, the operation setting values of the plurality of medical apparatuses are often changed in comparison with the phase other than the intraoperative phase, the nurse necessity degree judging portion 31g makes a judgment as above.

In the case of preparation or surgical incision closing to be the phase other than the intraoperative phase, the nurse necessity degree judging portion 31g of the priority degree setting portion 31e judges the support priority degree as "low" and does not add a comment.

Further, a display screen as shown in FIG. 11 is displayed on the display portion 43 of the terminal apparatus 6. Note that FIG. 11 shows an example of a display screen when the support priority degree is judged to be high. Other components are similar to those of the first embodiment.

Figure 12:
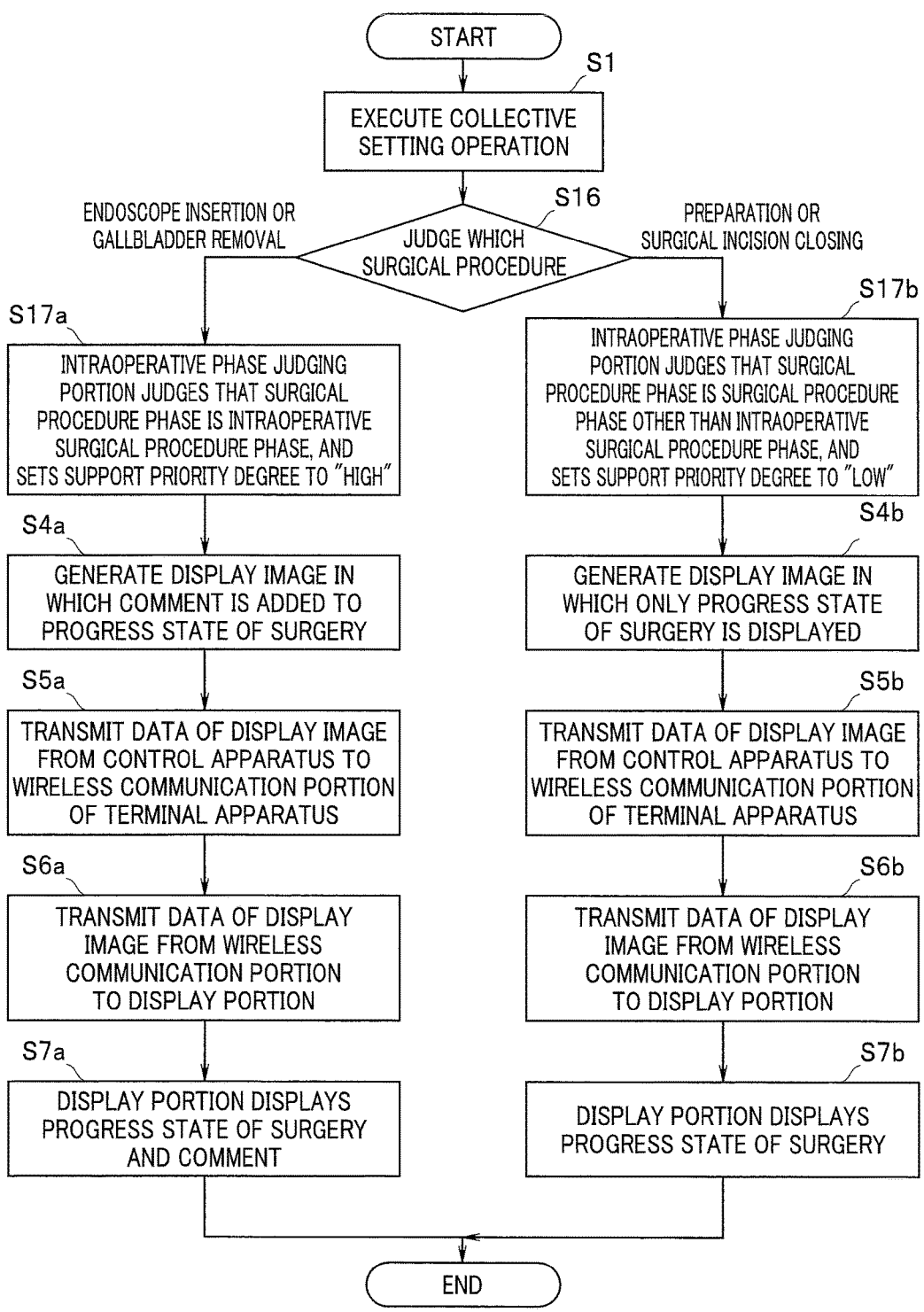
FIG. 12 is a flowchart showing operation content in the second embodiment.

Operation of the present invention is as in FIG. 12. Content of a process shown in FIG. 12 is such that steps S2, S3a and S3b in the process shown in FIG. 8A are changed so that steps S16, S17a and S17b are performed instead, respectively. Therefore, same processes as those in FIG. 8A are given same reference numerals, and description of the processes will be omitted.

When a collective setting operation is performed at step S1, the surgical procedure phase analyzing portion 31h judges which surgical procedure phase a surgical procedure phase for which the collective setting operation is executed corresponds to, at next step S16. In other words, the surgical procedure phase analyzing portion 31h judges which surgical procedure phase has been selected as the surgical procedure phase for which the collective setting operation is executed. The surgical procedure phase analyzing portion 31h sends the judged surgical procedure phase to the intraoperative phase judging portion 31i.

If the surgical procedure phase analyzing portion 31h judges that the surgical procedure phase is a surgical procedure phase of endoscope insertion or gallbladder removal, the intraoperative phase judging portion 31i judges that the surgical procedure phase is an intraoperative surgical procedure phase and sets the support priority degree to "high" at step S17a.

After step S17a, a process of steps S4a to S7a is performed. Display content of a comment displayed on the display portion 43 in this case is as shown in FIG. 11. Note that FIG. 11 shows the scene item of gallbladder removal as intraoperative progress state information. In a case of the scene item of endoscope insertion instead of the scene item of gallbladder removal in FIG. 11, content of other parts are same.

Though content of FIG. 11 is slightly different from content of FIG. 7, it is same that support by the nurse N is required. Therefore, the nurse N grasps necessity of support corresponding to the displayed comment and can easily give support.

On the other hand, if the surgical procedure phase analyzing portion 31h judges that the surgical procedure phase is the surgical procedure phase of preparation or surgical incision closing at step S16, the intraoperative phase judging portion 31i judges that the surgical procedure phase is the surgical procedure phase other than the intraoperative surgical procedure phase, and the priority degree setting portion 31e sets the support priority degree to "low".

After step S17b, the process of steps S4b to S7b is performed. In this case, similarly to the case of step S7b in FIG. 8A, the nurse N can grasp a progress state.

The present embodiment has an advantageous effect almost similar to that of the first embodiment. That is, according to the present embodiment, the nurse N carrying the terminal apparatus 6 displays the support priority degree information making it possible to easily judge which operating room the nurse N should preferentially go to in order to support a surgery in the operating room. Therefore, it is smoothly performed for the nurse N carrying the terminal apparatus 6 to support a surgery in an operating room requiring support by a nurse, and it becomes possible to perform the surgery efficiently.

Note that, in a case of performing the process of FIG. 12, a process of steps S8a to S14a may be performed after the process of step S7a, as shown in FIG. 8B.

Further, a configuration is also possible in which the first and second embodiments are combined. Further, the priority degree setting portion 31e may perform support priority degree judgment in each of the first and second embodiments, and judge the support priority degree to be highest if support priority degrees in both embodiments are "high" and "high", second highest if the support priority degrees are "high" and "low", or "low" and "high", and lowest if the support priority degrees are "low" and "low".

By the way, a configuration as in FIG. 13 may be adopted as a medical system. FIG. 13 shows a whole configuration of a medical system 1C. In the first operating room 2A, a first endoscopic surgical system 71A is installed. In the second and third operating rooms 2B and 2C, second and third endoscopic surgical systems 71B and 71C are installed, respectively.

The first endoscopic surgical system 71A is configured with: medical apparatuses such as a video processor 11a, a monitor 15a, a pneumoperitoneum apparatus 14a, a shadowless lamp 29a and an operating table 8a; a touch panel 72a for operating the medical apparatuses; and a first controller 4a configured to wiredly or wirelessly communicate with each of the medical apparatuses. First notification means (or first notification circuit) 35a capable of notifying information to an outside is provided inside the first controller 4a. Note that the first notification means 35a may be configured as a separate apparatus provided with an interface capable of wiredly or wirelessly communicating with the first controller 4a.

The second and third endoscopic surgical systems 71B and 71C are also provided with: a second controller 4b and a third controller 4c, and second notification means (or second notification circuit) 35b and third notification means (or third notification circuit) 35c, respectively, similarly to the first endoscopic surgical system 71A.

A terminal apparatus 73 is installed inside or outside the first to third operating rooms 2A to 2C and is provided with a display portion 73a configured to receive information notified from the first to third notification means 35a to 35c and show display corresponding to the information.

Figure 14:
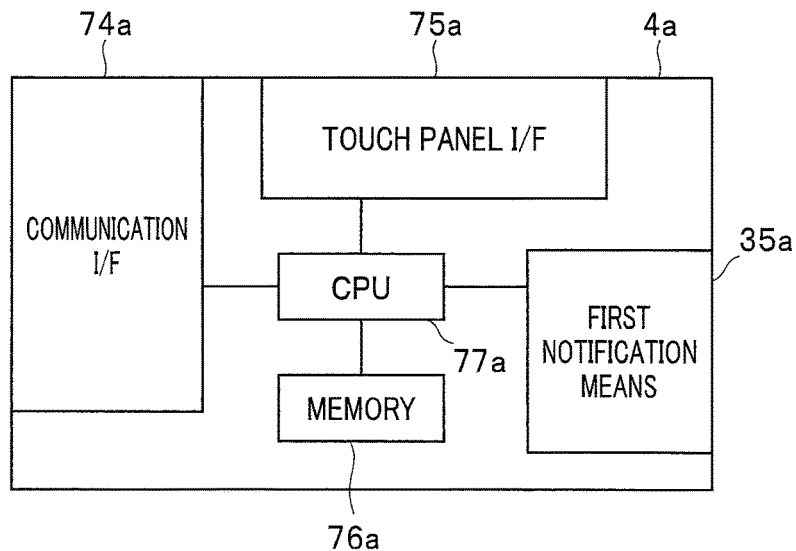
FIG. 14 is a diagram showing a configuration of a controller.

FIG. 14 shows an internal configuration of the first controller 4a. Note that the second and third controllers 4b and 4c are configured similarly to the first controller 4a. The first controller 4a is provided with a communication I/F 74a configured to communicate with the medical apparatuses, a touch panel I/F 75a connected to the touch panel 72a, the first notification means 35a configured to notify information to the outside and a memory 76a for storing various kinds of information, and the first controller 4a is controlled by a CPU 77a.

In the memory 76a, identification information specific to the first controller, setting information for separately (or simultaneously) controlling each of the apparatuses via communication, notification information notified to the outside via the first notification means 35a and the like are stored as data.

Figure 15:
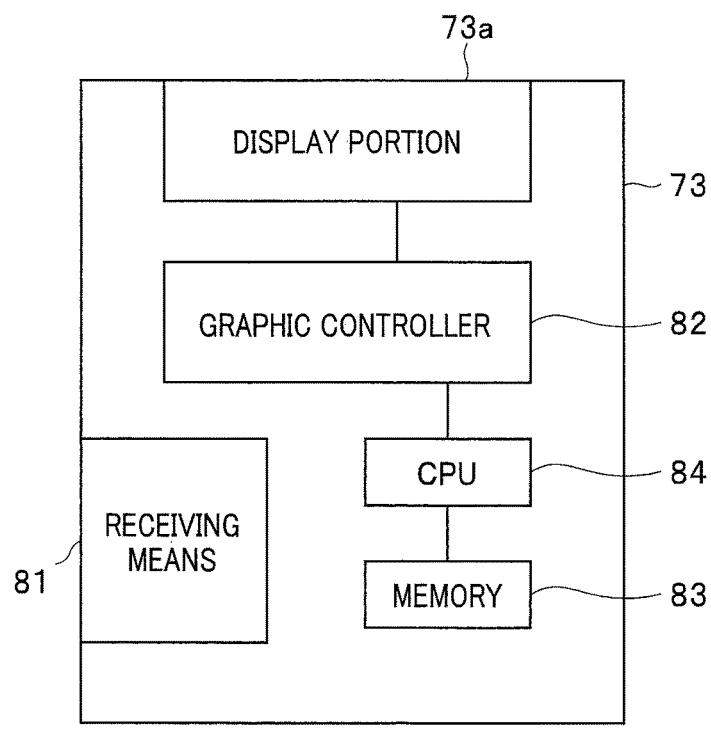
FIG. 15 is a diagram showing a configuration of the terminal apparatus.

FIG. 15 shows a configuration of an inside of the terminal apparatus 73. The terminal apparatus 73 is provided with receiving means (or receiving circuit) 81 configured to receive information notified from the first to third notification means 35a to 35c, a graphic controller 82 configured to control display of the display portion 73a, and a memory 83 for storing various kinds of information, and the terminal apparatus 73 is controlled by a CPU 84.

In the memory 83, information to be displayed in association with identification information specific to the terminal apparatus 73, display information for showing display corresponding to notification information and the like are stored as data.

Next, operation of the medical system 1C of FIG. 13 will be described.

For example, by showing a case where, in the first endoscopic surgical system 71A in the first operating room 2A in which the plurality of medical apparatuses are clearly shown, a predetermined operation of an apparatus related to an endoscopic surgery performed from the touch panel 72a is "stop air feeding of pneumoperitoneum apparatus", and a predetermined operation of an apparatus related to a laparotomy surgery performed from the touch panel 72a is "light up shadowless lamp" as an example, description will be made on operation of that case.

Figure 16:
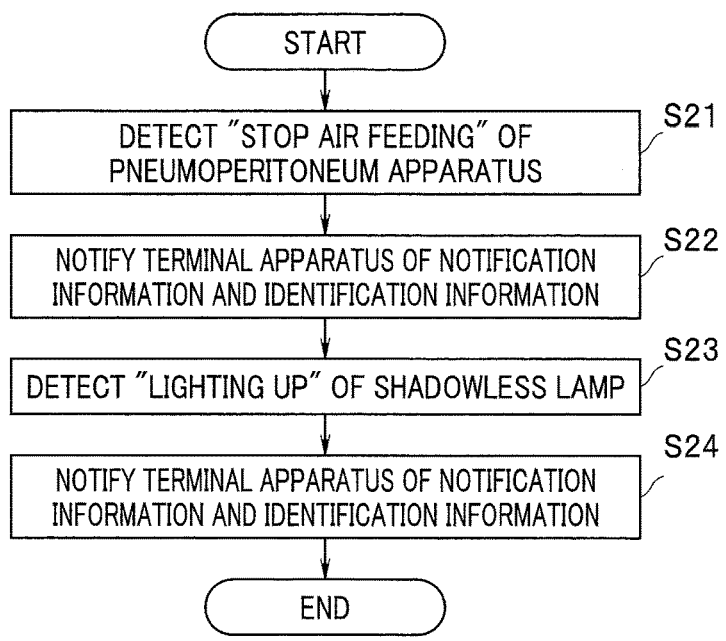
FIG. 16 is a flowchart showing a process of the controller notifying the terminal apparatus of information by an operation of a touch panel.

FIG. 16 shows a process flow illustrating a process performed until the terminal apparatus 73 is notified of notification information via the first notification means 35a when operations of stopping air feeding of the pneumoperitoneum apparatus 14a and lighting up the shadowless lamp 29a are sequentially performed.

At step S21, the first controller 4a detects that the operation of "stop air feeding" of the pneumoperitoneum apparatus 14a has been performed with the touch panel 72a.

At step S22, the first controller 4a notifies the terminal apparatus 73 of notification information related to "stop air feeding" and identification information via the first notification means 35a.

At step S23, the first controller 4a detects that the operation of "lighting up" of the shadowless lamp 29a has been performed with the touch panel 72a.

At step S24, the first controller 4a notifies the terminal apparatus 73 of notification information related to "lighting up" and identification information via the first notification means 35a.

Figure 17:
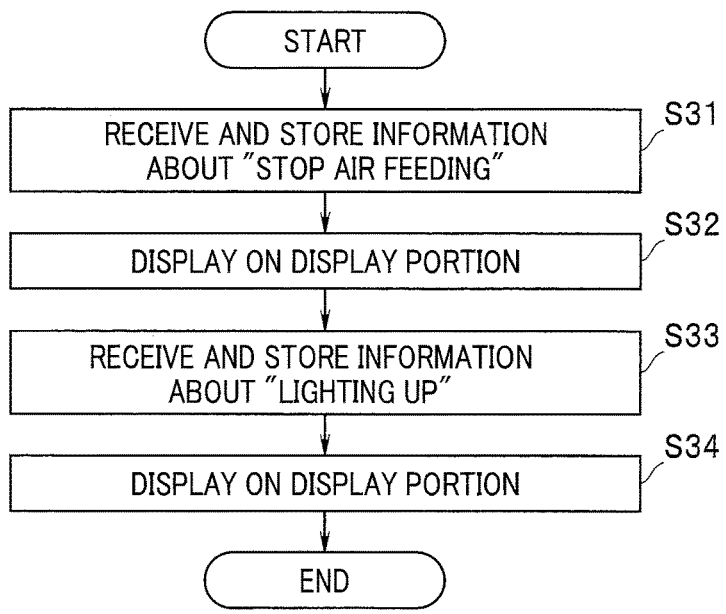
FIG. 17 is a flowchart showing a process performed in a case where the information is notified from the controller.

FIG. 17 shows a second process flow performed until the terminal apparatus 73 receives the notification information related to "stop air feeding" and the notification information related to "lighting up" sequentially and shows a predetermined display.

At step S31, the terminal apparatus 73 receives the notification information about "stop air feeding" and the identification information via the receiving means 81 and stores the notification information and the identification information into the memory 83.

Figure 18:
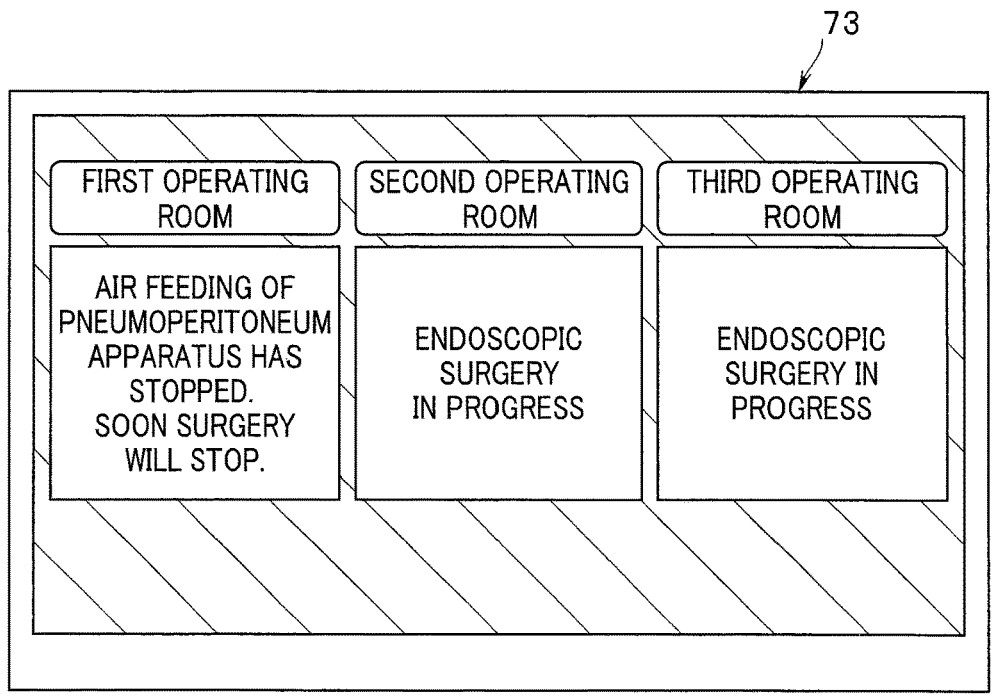
FIG. 18 is a diagram showing an example of a display screen of the terminal apparatus corresponding to the process of FIG. 17.

At step S32, the terminal apparatus 73 analyzes the stored notification information and identification information, reads out predetermined display information from the memory 83 and displays the display information on the display portion 73a (see FIG. 18).

At step S33, the terminal apparatus 73 receives the notification information about "lighting up" and the identification information via the receiving means 81 and stores the notification information and the identification information into the memory 83.

Figure 19:
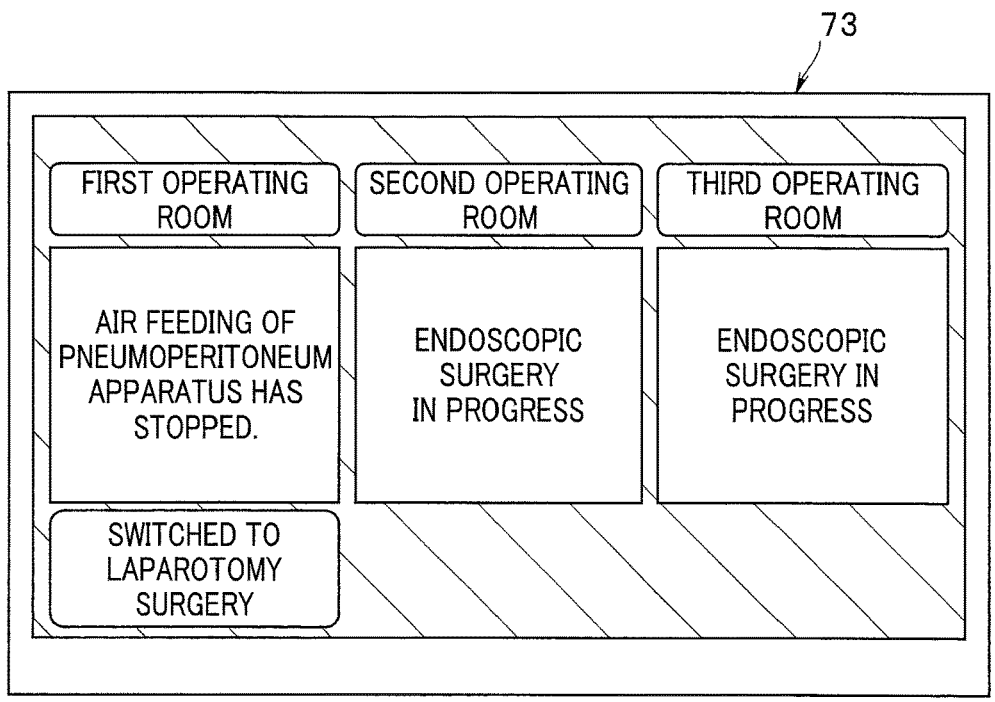
FIG. 19 is a diagram showing an example of the display screen of the terminal apparatus corresponding to the process of FIG. 17.

At step S34, the terminal apparatus 73 analyzes the stored notification information and identification information, reads out predetermined information from the memory 83 and displays the display information on the display portion 73*a* (see FIG. 19).

FIG. 18 is a diagram showing an example of display on the terminal apparatus 73 at step S32. For example, if, when the first to third operating rooms 2A to 2C are in a state that "endoscopic surgery in progress" is displayed, a result of analyzing the notification information and the identification information is "stop air feeding" notified from the first controller 4*a* installed in the operating room 2A, the display shown in FIG. 18 is displayed.

FIG. 19 is a diagram showing an example of display on the terminal apparatus 73 at step S34. For example, there may be a case where a surgery by endoscope is switched to a laparotomy surgery when it is judged that the surgery by endoscope is difficult. When lighting up of a shadowless lamp used for the laparotomy surgery is received, the display shown in FIG. 19 is displayed.

In the medical system 1C shown in FIG. 13, operation information is automatically notified only by operating an apparatus with the touch panel, and the progress state of the surgery is displayed. Therefore, the medical system 1C has an advantageous effect that it is possible to grasp the progress state of the surgery without entering the operating room.

Next, a first modification of the medical system 1C of FIG. 13 will be described. A configuration of the present modification is similar to that of FIG. 13.

Next, operation of the present modification will be described with regard to a case of the first operating room 2A.

Figure 20:
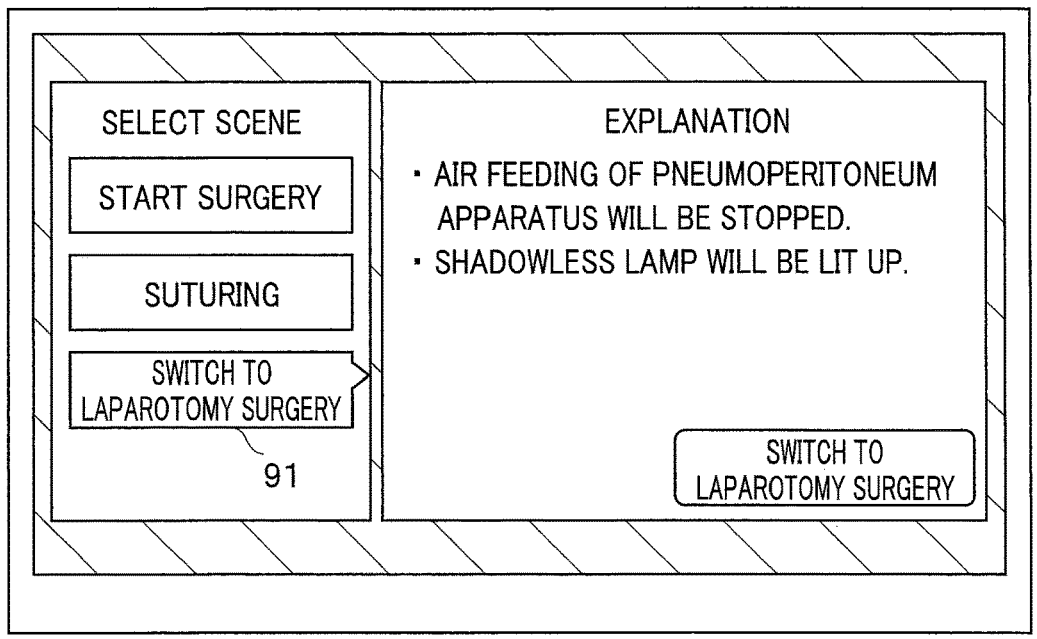
FIG. 20 is a diagram showing an example of an operation screen of the touch panel in a first modification of the medical system of FIG. 13.

FIG. 20 is a diagram showing a first example of a touch panel operation screen showing an example of an operation screen to be displayed on a first touch panel 72*a*.

In the operation screen example, the first controller 4*a* displays a "switch to laparotomy surgery" button 91 on the touch panel 72*a*. The first controller 4*a* stores setting information for collectively setting medical apparatuses required at time of switching to a laparotomy surgery, in the memory 76*a*.

When the "switch to laparotomy surgery" button 91 displayed on the operation screen of the touch panel 72*a* is pressed, the pneumoperitoneum apparatus 14*a* is controlled through communication to stop air feeding, and the shadowless lamp 29*a* is controlled through communication to be lit up.

Figure 21:
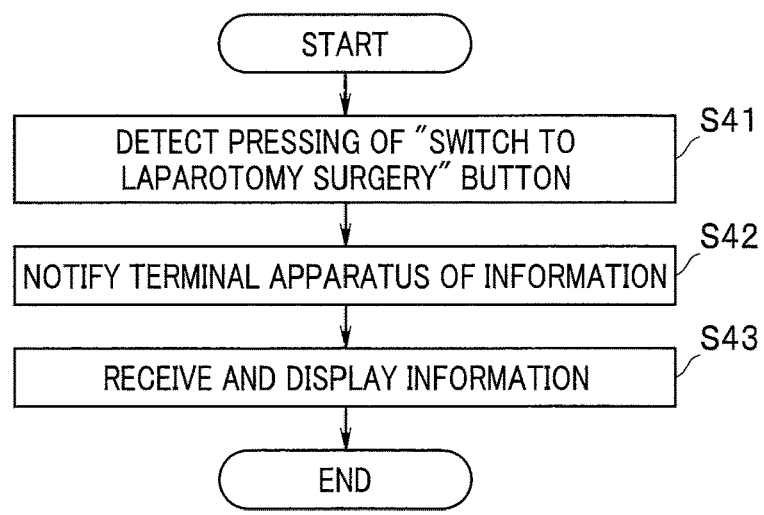
FIG. 21 is a flowchart showing a process of the controller corresponding to an operation by the operation screen of FIG. 20.

FIG. 21 is a third process flow illustrating a process performed until the terminal apparatus 73 is notified of notification information when the "switch to laparotomy surgery" button 91 shown in FIG. 20 is pressed.

At step S41, the first controller 4*a* detects that the "switch to laparotomy surgery" button 91 has been pressed.

At step S42, the first controller 4*a* notifies the terminal apparatus 73 of notification information about "switch to laparotomy surgery" and identification information via the first notification means 35*a*.

At step S43, the terminal apparatus 73 receives the notification information about "switch to laparotomy surgery" and the identification information via the receiving means 81, reads out predetermined display information from the memory 83 and displays the display information.

For example, if a result of analyzing the notification information and the identification information is "switch to laparotomy surgery" notified from the first controller 4*a* installed in the operating room 2A when all the pneumoperitoneum apparatuses in the first to third operating rooms 2A to 2C are feeding air, the display shown in FIG. 19 is displayed.

According to the present modification, in addition to the advantageous effect of the medical system 1C of FIG. 13, it is possible to grasp whether a surgery will end soon or much time is required because of switching to a laparotomy surgery, without a time lag (time delay), because it is possible to grasp termination of an endoscopic surgery (example: stop air feeding of pneumoperitoneum apparatus) and switching to a laparotomy surgery (example: light up shadowless lamp) without a time difference by causing switching to laparotomy and a related collective setting operation to be linked.

Next, a second modification of the medical system 1C of FIG. 13 will be described. A configuration of the present modification is similar to that of FIG. 13.

Next, operation of the present modification will be described with regard to the case of the first operating room 2A.

Figure 22:
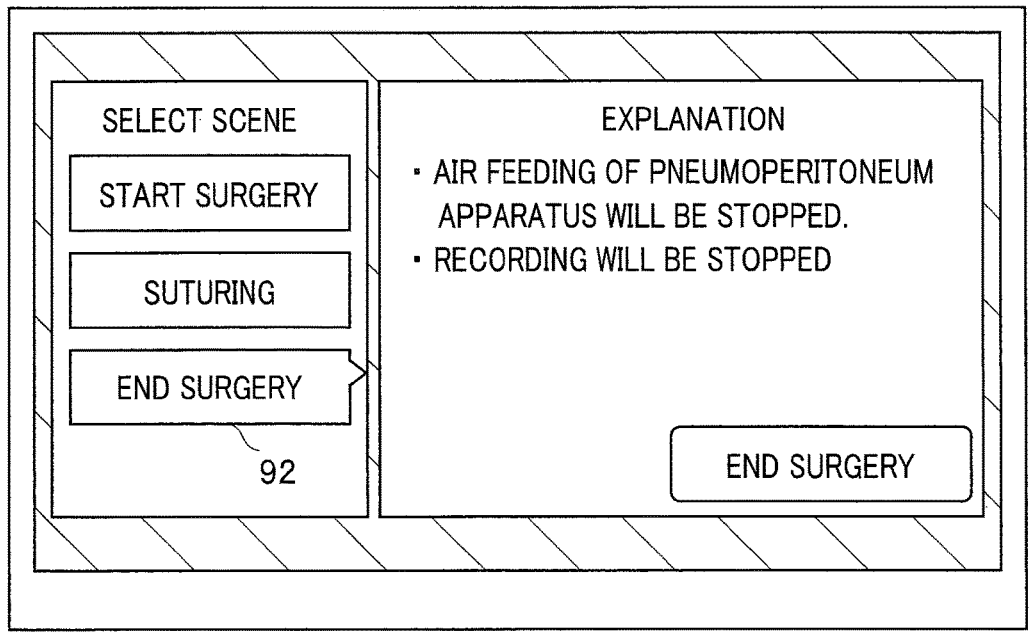
FIG. 22 is a diagram showing an example of an operation screen of the touch panel in a second modification of the medical system of FIG. 13.

FIG. 22 shows a second example of the touch panel operation screen showing an example of the operation screen to be displayed on the first touch panel.

In the display example of the operation screen, the first controller 4*a* displays a "end surgery" button 92 on the first touch panel 72*a*. The first controller 4*a* stores setting information making it possible to collectively perform operations of the medical apparatuses to be performed when a surgery ends, in the memory 76*a*. When the "switch to laparotomy surgery" button 91 displayed on the operation screen of the first touch panel 72*a* is pressed, the pneumoperitoneum apparatus 14*a* is controlled through communication to stop air feeding, and a recording apparatus not shown is controlled through communication to stop recording.

Figure 23:
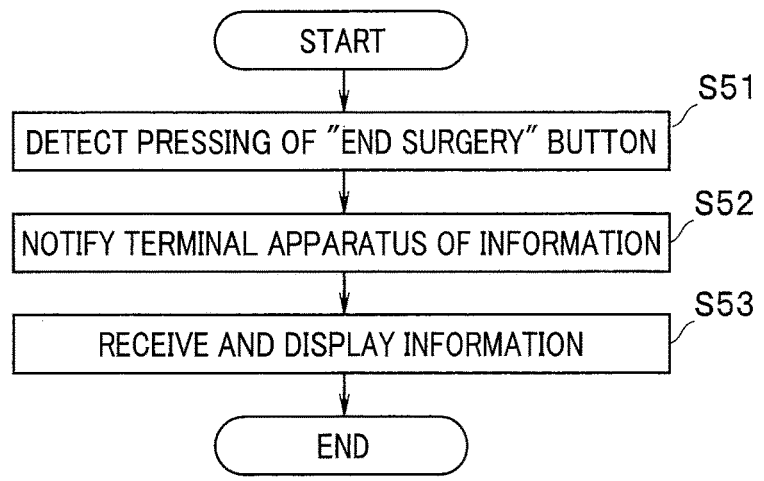
FIG. 23 is a flowchart showing a process of the controller corresponding to an operation by the operation screen of FIG. 22.

FIG. 23 shows a process flow illustrating a process performed until the terminal apparatus 73 is notified of notification information when the "end surgery" button 92 shown in FIG. 22 is pressed.

At step S51, the first controller 4*a* detects that the "end surgery" button 92 has been pressed.

At step S52, the first controller 4*a* notifies the terminal apparatus 73 of notification information about "end surgery" and identification information via the first notification means 35*a*.

Figure 24:
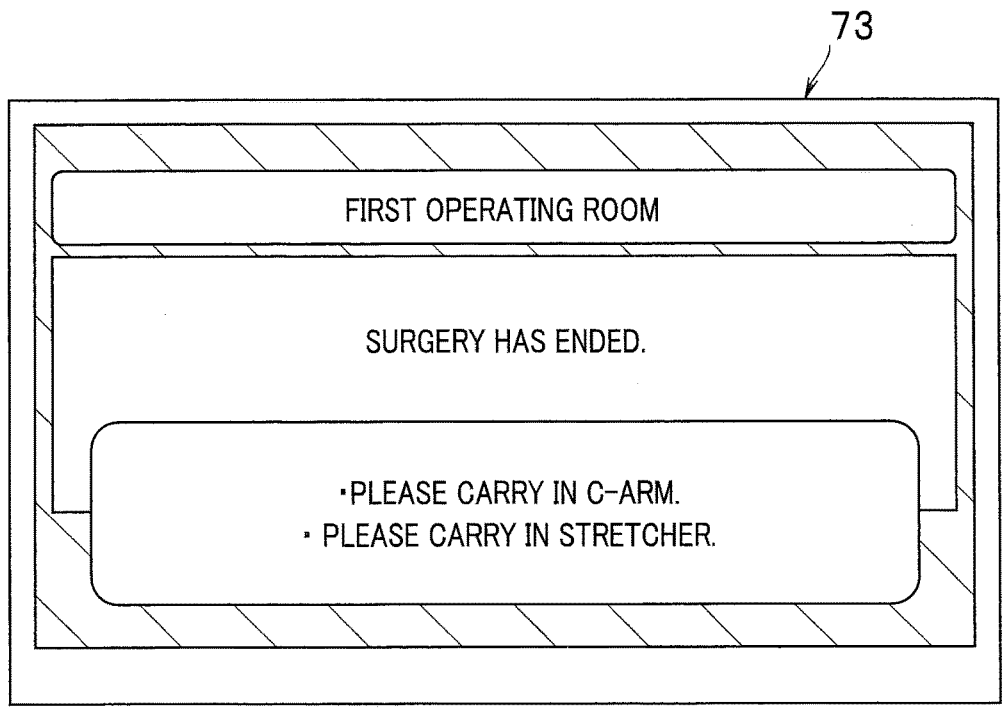
FIG. 24 is a diagram showing an example of display on the display screen of the terminal apparatus in the process of FIG. 23.

At step S53, the terminal apparatus 73 receives the notification information about "end surgery" and the identification information via the receiving means 81, reads out predetermined display information from the memory 83 and displays the display information (see FIG. 24 as a display example).

FIG. 24 shows an example of display on the terminal apparatus 73 at step S53. For example, if a result of analyzing the notification information and the identification information is "end surgery" notified from the first controller 4*a* installed in the first operating room 2A, information about mechanical equipment to be prepared, such as a C-arm for confirming that gauze or a medical appliance is not left in a body and a stretcher for carrying a patient to an outside of the operating room, is displayed.

According to the present modification, in addition to the advantageous effect of the medical system 1C of FIG. 13, it is possible to grasp (efficiently prepare) information about mechanical equipment to be prepared at a surgery end phase.

Next, a third modification of the medical system 1C of FIG. 13 will be described. The present modification has the same configuration as the medical system 1C of FIG. 13.

Next, operation of the present modification will be described.

Figure 25:
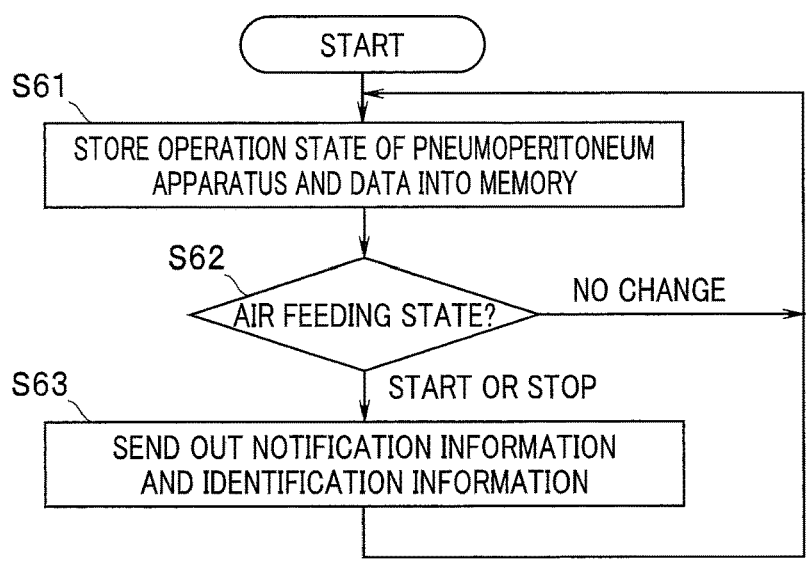
FIG. 25 is a flowchart showing a process of the controller detecting change in an operation state of a pneumoperitoneum apparatus and notifying the terminal apparatus of the change in a third modification of the medical system of FIG. 13.

FIG. 25 shows a process flow performed until, for example, in the first endoscopic surgical system 71A in the first operating room 2A, the first controller 4a detects change in an operation state of the pneumoperitoneum apparatus 14a and notifies the terminal apparatus 73 of notification information.

At step S61, the first controller 4a receives data from which the operation state can be recognized, from the pneumoperitoneum apparatus 14a via the communication I/F 74a and stores the data into the memory 76a.

At step S62, the CPU 77a inside the first controller 4a analyzes the obtained data, compares the data with judgment information for judging whether notification is necessary or not, which is stored in advance. The CPU 77a returns to the process of step S61 if judging that notification is unnecessary, and proceeds to step S63 if judging that notification is necessary.

For example, since an actually measured value of abdominal cavity pressure continuously changes due to influence of pressure given to an abdominal region by a medical appliance a surgeon is using for surgery or by influence of a patient's breathing, it is judged that notification is unnecessary, regarding an air feeding state itself as not having changed. On the other hand, in a case of a change in a state of start/stop of air feeding it is judged that notification is necessary.

At step S63, the CPU 77a in the first controller 4a reads out notification information corresponding to a result of the judgment and identification information specific to the first controller 4a from the memory 76a and sends out the notification information and the identification information to the terminal apparatus 73 via the first notification means 35a.

Figure 26:
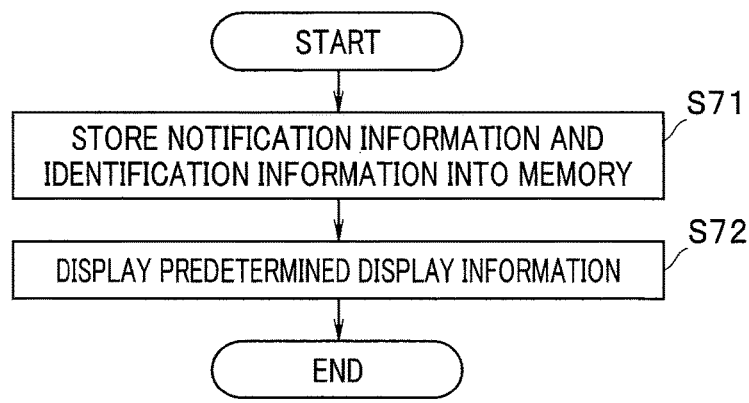
FIG. 26 is a flowchart showing a process of the terminal apparatus receiving and displaying the notified notification information.

FIG. 26 shows a process flow illustrating a process performed until the terminal apparatus 73 receives and displays the notification information.

At step S71, the terminal apparatus 73 receives the notification information and identification information notified from the first notification means 35a of the first controller 4a via the receiving means 81 and stores the notification information and the identification information into the memory 83.

Figure 27:
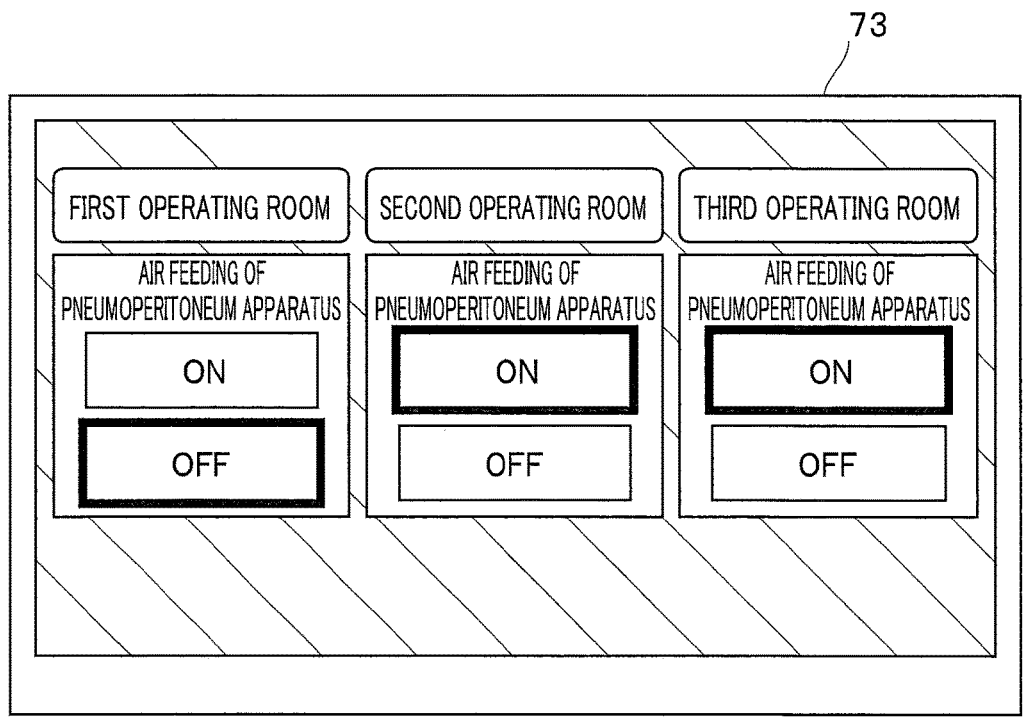
FIG. 27 is a diagram showing an example of display on the display screen of the terminal apparatus.

At step S72, the CPU 84 inside the terminal apparatus 73 reads out predetermined display information from the memory 83 and displays the display information on the display portion 73a (see FIG. 27 for a display example).

FIG. 27 shows a display example of the terminal apparatus 73.

The terminal apparatus 73 displays air feeding states of the pneumoperitoneum apparatuses in the first to third operating rooms 2A to 2C. When the pneumoperitoneum apparatuses of the second and third operating rooms 2B and 2C are feeding air, ON displays are highlighted (displayed in thick frames in FIG. 27). When air feeding of the pneumoperitoneum apparatus 14a of the first operating room 2A is stopped, an OFF display is highlighted.

According to the present modification, it is possible to simply grasp a state of a surgery without entering an operating room, by making it possible to monitor a state of operation in conjunction with an operation of a pneumoperitoneum apparatus.

Note that an embodiment or the like configured by partially combining the embodiments and the like described above also belongs to the present invention.

What is claimed is:

1. A medical system comprising:
a plurality of medical apparatuses used for surgery using an endoscope;
a control device configured with hardware and configured to communicate with the plurality of medical apparatuses, the control device including a storage device for storing operation setting values for causing the plurality of medical apparatuses to operate, the operation setting values being set along a procedure for the surgery,
the control device being configured to:
  store progress state information indicating progress of the surgery,
  set information about a height of necessity degree of a nurse to support the surgery as information about a support priority degree for smoothly advancing the surgery, and
  transmit the progress state information;
a voice input device provided with a microphone capable of making a collective setting for the operation setting values of the plurality of medical apparatuses by a voice input from a sterile area;
an operation panel capable of making the collective setting for the operation setting values of the plurality of medical apparatuses by touch operation from a non-sterile area where the plurality of medical apparatuses are arranged;
and
a terminal device configured with hardware and configured to receive the progress state information transmitted from the control device; and
display the received progress state information; wherein
the control device identifies a scene item to be transmitted as the progress state information by referring to a look up table stored as information about a corresponding relation between scene items set along the procedure for the surgery and operation setting values being collectively set by either the voice input device or the operation panel, acquires a judgment result indicating that the support priority degree is high when the operation setting values of the medical apparatuses are collectively set by the voice input device in comparison with a case where the operation setting values are collectively set by the operation panel, and transmits information about the support priority degree corresponding to the acquired judgment result so that the information about the support priority degree is added to the progress state information, and
the terminal device displays the information about the support priority degree together with the progress state information.

2. The medical system according to claim 1, wherein
the terminal device returns reply data to the control device after a process of displaying the information about the necessity degree of the nurse; and
the control device judges the reply data returned from the terminal device and changes the information about the height of the necessity degree of the nurse according to a judgment result.

3. The medical system according to claim 1, wherein
the control device sets the support priority degree when the plurality of medical apparatuses are operated with the operation setting values collectively set by either the voice input device or the operation panel, and adds the information about the support priority degree to the progress state information, according to a result of setting the support priority degree.

4. The medical system according to claim 1, wherein
the terminal device further comprises an operation button for a reply, and, if the operation button is operated, sends a reply signal of the operation button to the control device; and
the control device changes set content of the support priority degree before the reply signal according to the reply signal.

5. The medical system according to claim 1, wherein
the plurality of medical apparatuses include a light source configured to supply illuminating light to the endoscope; a signal processor configured to perform signal processing for an image pickup device mounted on the endoscope; a pneumoperitoneum device configured to perform pneumoperitoneum of a body into which the endoscope is inserted, with gas; a display device configured to display an image signal generated by the second device as an endoscopic image; and an electrical energy supply configured to supply electrical energy for performing treatment to an treatment instrument for performing treatment.

6. The medical system according to claim 1, comprising the plurality of medical apparatuses, the voice input device, the operation panel, and the control device arranged in each of first and second operating rooms, wherein
the control device in one of the first and second operating rooms adds the information about the support priority degree set based on collective setting by the voice input device or the operation panel in the one operating room and number information identifying the one operating room to the progress state information, and
the terminal device displays the information about the support priority degree together with the progress state information and the number information.

7. The medical system according to claim 1, wherein
the control device wirelessly transmits the progress state information and the information about the support priority degree, and
the terminal device wirelessly receives the progress state information and the information about the support priority degree.

* * * * *